(12) United States Patent
Gombrich et al.

(10) Patent No.: US 6,663,576 B2
(45) Date of Patent: Dec. 16, 2003

(54) CERVICAL SCREENING SYSTEM

(75) Inventors: Peter P. Gombrich, Chicago, IL (US); Richard A. Domanik, Libertyville, IL (US); George Gorodeski, Beechwood, OH (US)

(73) Assignee: Molecular Diagnostics, Inc., Chicago, IL (US)

( * ) Notice: Subject to any disclaimer, the term of this patent is extended or adjusted under 35 U.S.C. 154(b) by 46 days.

(21) Appl. No.: 09/725,333

(22) Filed: Nov. 29, 2000

(65) Prior Publication Data

US 2001/0029044 A1 Oct. 11, 2001

Related U.S. Application Data

(60) Provisional application No. 60/172,401, filed on Dec. 17, 1999, provisional application No. 60/167,831, filed on Nov. 29, 1999, and provisional application No. 60/183,140, filed on Feb. 17, 2000.

(51) Int. Cl.[7] ............................................. A61B 10/00
(52) U.S. Cl. ..................................................... 600/562
(58) Field of Search ........................... 600/562, 563–572

(56) References Cited

U.S. PATENT DOCUMENTS 3,664,328 A 5/1972 Moyle, Jr.
4,633,886 A 1/1987 Bucaro, Jr.
5,231,992 A 8/1993 Leon
5,741,648 A 4/1998 Hemstreet, III et al.

FOREIGN PATENT DOCUMENTS

DE  28 29 118       1/1980
WO  WO 91/16004    10/1991

OTHER PUBLICATIONS

R.H.C. Benthall, 1969, *The Lancet*, 574–575, "Suction Amnioscope".

Evans et al., 1969, *Acta Cytologica*, 13:119–121, "A Membrane Cytologic Technique for Assessing the Extent of Ectocervical Carcinoma Using the Tenovus Applicator".

International Search Report for PCT/US00/32504.

*Primary Examiner*—Max F. Hindenburg
*Assistant Examiner*—Pamela L Wingood
(74) *Attorney, Agent, or Firm*—Merchant & Gould P.C.

(57) ABSTRACT

A system for accurately obtaining cervical cells from a patient and quickly screening the sample includes a collector for collecting a spatially arranged cell sample from a target tissue, and an analyzer that examines the cell sample for abnormal cells while the cell sample remains on a surface of the collector.

20 Claims, 16 Drawing Sheets

CERVICAL SCREENING SYSTEM

RELATED APPLICATIONS

This application claims priority to provisional application Ser. No. 60/172,401, filed Dec. 17, 1999, entitled "INSTRUMENT FOR ANALYZING TISSUE COLLECTED BY IN-VIVO SAMPLE COLLECTOR", provisional application Ser. No. 60/167,831, filed Nov. 29, 1999, entitled "CERVICAL TISSUE SAMPLE COLLECTOR HAVING A FLUID DISPENSER AND CONTAINER", U.S. Ser. No. 60/167,831, and provisional application Ser. No. 60/183,140, filed Feb. 17, 2000, entitled "CELL RECOVERY DEVICE". Each of these provisional applications are specifically incorporated by reference herein.

This application is related to utility patent applications "ANALYSIS INSTRUMENT", and "PHYSICIAN'S COLLECTOR", each application filed on the even date herewith and each application specifically incorporated by reference herein.

BACKGROUND

Cervical cancer is a leading form of cancer among women. In the United States alone, there are believed to be more than two million cases of precancerous cervical abnormalities annually. The U.S. also sees, on average, about sixty five thousand cases of cervical carcinoma and about sixteen thousand cases of invasive cervical cancer. Although screening is less common outside the Unites States, nearly half a million cases of cervical cancer are detected each year around the world.

Cervical cancer frequently begins as a precancerous lesion of the cervix. These lesions are also known as cervical intraepithelial neoplasia. If left untreated, these lesions can deepen over time and ultimately develop into an invasive cancer of the cervix and associated tissues. Fortunately, early detection followed by appropriate treatment results in a very high cure rate for cervical cancer.

Therefore, it is quite important that at least certain factions of the female population undergo regular screening. These factions include patients with previous cervical abnormalities and those who have a family history of cervical abnormalities. Women who are sexually active are at greater risk and should undergo regular screening, as are those who test positive for HPV (human papillomavirus). This is a sexually transmitted virus that in some forms can cause genital warts.

During the 1940's, Dr. George Papanicolaou developed a screening test which bears his name and which has become the most widely used screening technique for detecting abnormal cervical cells. Today, this test is known more commonly as the PAP test or the PAP smear test. Typically, the PAP test is performed in the physician's office as part of a woman's routine gynecological examination. The test involves collecting cervical cells via a brush, stick or swab that is used to loosen and then collect cells that can be examined microscopically.

Cervical samples taken for the purposes of Pap testing are deposited on a planar microscope slide, fixed to prevent cell loss or degradation, and stained in a manner that accentuates and differentiates the various cellular structures. These prepared samples are subjected to detailed microscopic evaluation by a cytotechnologist or pathologist to detect and classify any cellular abnormalities that may be present in the cells deposited on the microscope slide. The results of these evaluations are reported to the attending physician who determines whether additional evaluation or treatment of the patient is required.

The Pap test as it is currently practiced is time consuming and requires a highly skilled supporting infrastructure. Even in countries with the necessary infrastructure, several weeks can elapse between taking the sample and reporting the results of the evaluation to the attending physician. The uncertainty attendant in this delay is stressful to the patient. As it is not practical or the patient to be retained at the medical facility until the results of the evaluation have been returned, it is necessary for the attending physician to contact the patient to inform them that the results of the test were negative or, conversely, if the results were positive, to arrange for a follow-up visit.

In the US, fewer than 60% of the patients contacted with positive results actually present themselves for follow-up evaluations or treatment. This percentage is lower in other countries and is particularly low in public health screening programs and clinics that deal predominantly with transient populations and populations that are remote from the site of testing. Furthermore, depending upon the particular patient population, between 50 and 90 percent of all Pap samples taken are determined to contain no evidence of cellular abnormalities. This high percentage of negative samples imposes a substantial burden on the health care system and diverts resources from making cervical screening tests more widely available.

It is therefore desirable to provide a means of cervical screening that can produce a determination of whether a sample does or does not contain evidence of cellular abnormalities within the time frame of a typical cervical examination. As such a means provides the test results before the patient leaves the examination area, the uncertainty and stress of waiting for a negative diagnosis is eliminated and patients showing positive results can be retained for immediate follow-up and treatment.

Identifying those patients showing no signs of cellular abnormalities at the time of the initial examination also reduces the number of samples that must be sent to a laboratory for evaluation. This reduces the non-productive burden on the health care system and frees resources that can be used to increase the availability of cervical screening and other diagnostic testing.

The manner in which a positive result is followed up varies substantially by country. In some countries such as the U.S., a finding of ASCUS (atypical squamous cells of undetermined significance) or higher is generally considered to be grounds for follow-up or medical intervention. In other countries, the standard of care is to follow up or intervene in cases where the detected degree of abnormality corresponds to LSIL (low-grade squamous intraepithelial lesions) or HSIL (high-grade squamous intraepithelial lesions) and higher, but, in recognition that many lower grade abnormalities are benign or revert to normal over time, to ignore lower grade detected abnormalities. It is therefore desirable to be able to establish a reporting threshold that is consistent with the prevailing standard of care.

Cervical abnormalities generally present in the form of lesions or localized clusters of abnormal cells. The sampling methods utilized in current cervical screening procedures acquire cells from these lesions, but then disperse these cells into a typically much larger number of normal cells obtained from outside of the boundaries of the lesion. This dispersion results in the evaluation of a conventional cervical sample being an exercise in the detection of a rare event, that is, finding one or a few abnormal cells within a background consisting of a very large number (50,000–300,000) of normal cells. Dispersion also precludes using the sample to determine the location of the lesion on the cervix.

It is therefore desirable that a means of sampling and evaluation be provided that retains the spatial relationships that exist between the cells in-vivo. Retaining these relationships effectively eliminates dispersion and allows mapping of the test results onto the cervix for the purpose of guiding follow-up or intervention.

SUMMARY

Accordingly, the invention is found in a system whereby cervical cells can be accurately and sufficiently obtained from a patient and can subsequently be quickly screened to determine if further analysis is warranted. The invention is found in a system in which cervical cells can be sampled in a way that maintains the spatial orientation in which the cells are located prior to sampling.

Therefore, the invention is directed to a cell analysis system that includes a collector for collecting a spatially arranged cell sample from a target tissue, and an analyzer that examines the cell sample for abnormal cells while the cell sample remains on a surface of the collector.

Other features and advantages of the present invention will be apparent from the following detailed description and drawings.

DETAILED DESCRIPTION OF THE PREFERRED EMBODIMENTS

Figure 1:
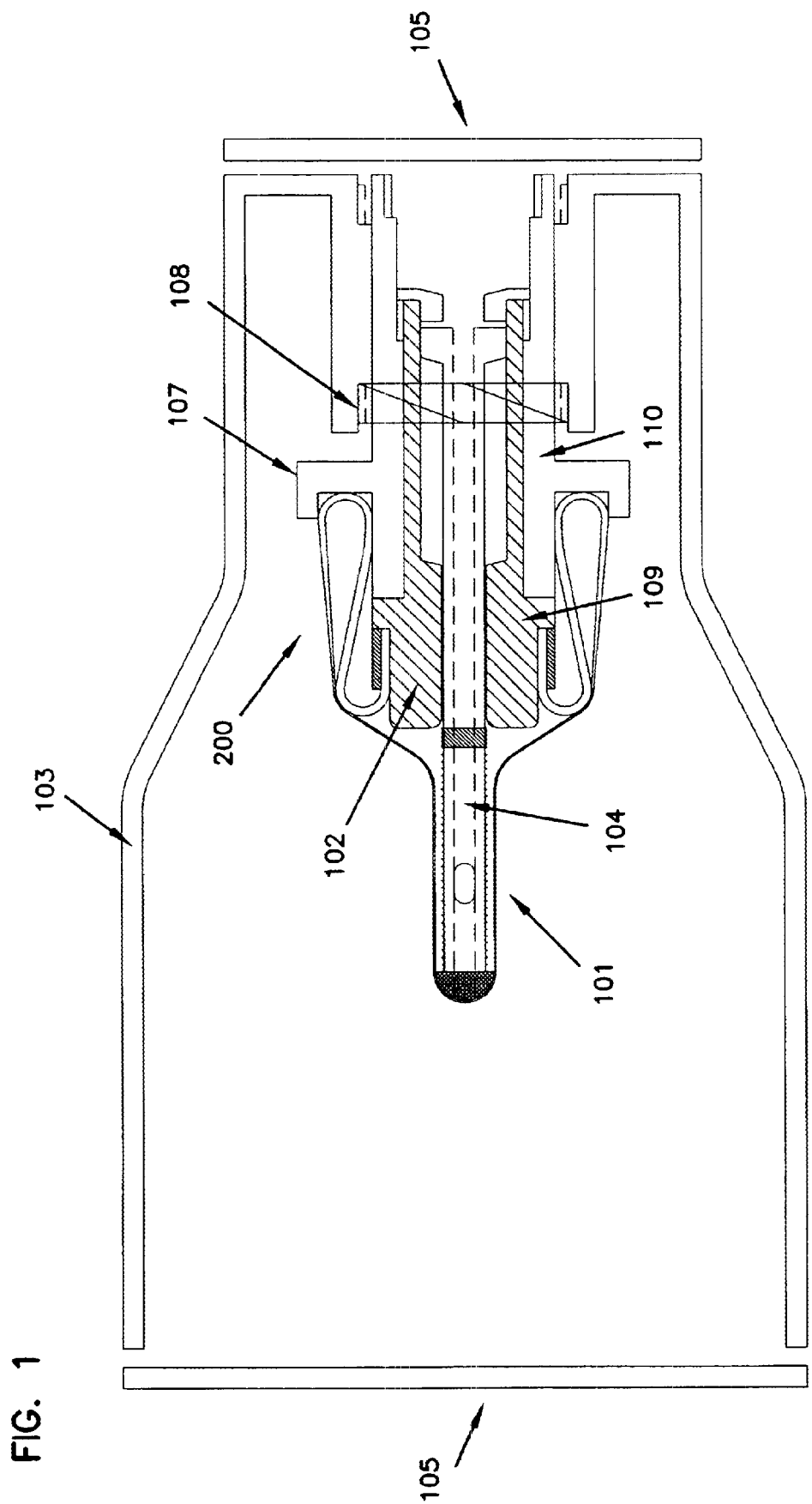
FIG. 1 is a sectional view of a physician's collector in accordance with a particular embodiment of the present invention. This Figure shows the compliant cell sampling member in a folded state prior to use.

The present invention is best understood with reference to the Figures, in which similar reference numbers are used to refer to similar elements in multiple Figures. FIG. 1 shows a particular embodiment of the present invention. The physician's collector includes a compliant cell sampling member 101 that is attached to an interface element 102 and that is mounted within a multifunctional container 103. A stylette 104 passes through the interface element 102 and into the cell sampling member 101 where it is bonded to the interior of the tip of the cell sampling member 101.

When the physician's collector is delivered to a clinician, it is preferred that the ends of the multifunctional container 103 be closed by suitable covers 105 that can be held in place by a shrinkable sleeve that incorporates a perforated tear strip (not illustrated). If desired, human and machine readable labeling such as a serial number of the physician's collector, expiration date and other relevant data can be provided on an exterior surface of the physician's collector.

The sampling member 101 as illustrated in FIG. 1 is preferably a balloon structure 200 that is made of a suitable elastomeric material such as silicone rubber, latex rubber, polyurethane or a thermoplastic elastomer. Alternatively, the sampling member 101 can include a compliant solid body such as a graded density foam. For the balloon embodiment, the wall thicknesses and other parameters are controlled during fabrication to obtain a desired pliability. In a preferred embodiment, the balloon structure is created using an injection molding process or similar process that provides for the preferred control over local wall thickness.

Figure 2:
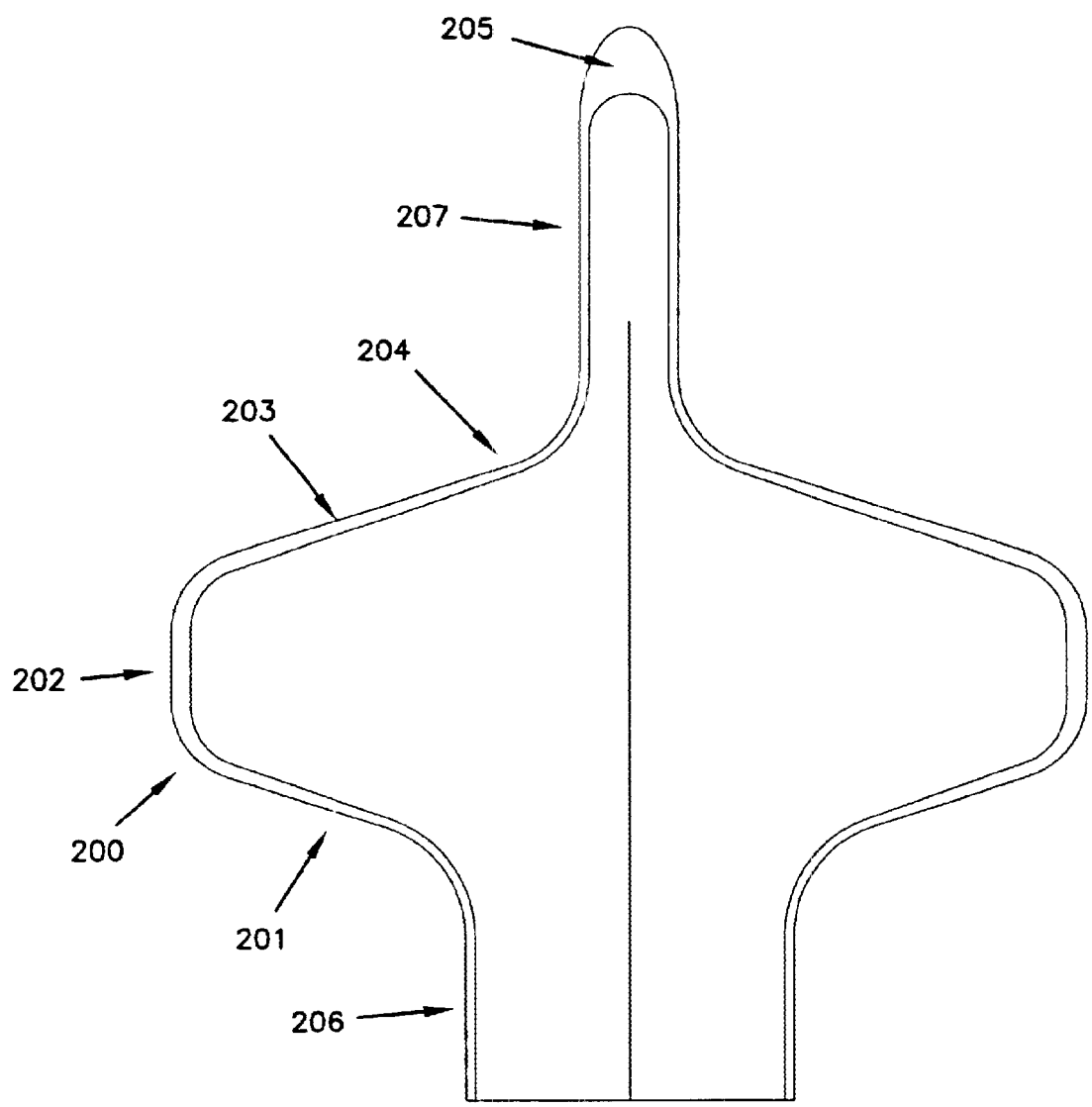
FIG. 2 is a sectional view of a compliant cell sampling member, illustrating the relative wall thicknesses of the sampling member in accordance with a particular embodiment of the present invention.

FIG. 2 provides an example of a balloon 200 in which the wall thicknesses vary with position. Preferably, the rear walls 201 and the side walls 202 have a relatively constant thickness that is greater than the rest of the balloon 200. The front wall 203 preferably tapers from a maximum thickness at the side wall 202 to a minimum value at the root 204 of the tip of the structure 200. Preferably, this minimum thickness is employed over most of the length of the tip of the balloon 200 where the thickness is again increased. In a particular embodiment, the neck 206 of the balloon 200 is also thinner than the rear wall 201.

Each wall thickness variation illustrated in FIG. 2 is intended to impart specific behavioral and performance properties to the balloon 200. For example, the substantial thickening at the tip 205 is intended to facilitate insertion of the tip into the cervical canal and to provide an anchoring site for the stylette 104. Further, the thick rear wall 201 and side walls 202 function as a spring that helps drive the deployment of the sampling member 101 from its folded state. Moreover, the thick rear and side walls 201, 202, respectively, help provide the stiffness beneficial in communicating forces from the handle 301 to the sampling member 101 and to resist expansion when air is introduced into the balloon 200. The sampling member 101 can be biased to an inflated sampling configuration, or the sampling member 101 can be biased to a deflated insertion and removal configuration.

The thick side walls 202 provide a ring that causes the thinner front wall 203 to drape over the cervix when the tip region 207 of the balloon structure 200 is constrained by the cervical canal and the ring is brought into contact with the cervix by pressure applied via the handle 301. The angle between the front wall 203 and the axis of the balloon is preferably chosen to minimize the change in the area of the front wall 203 that occurs during the draping process and thus to minimize the potential for forming wrinkles in the draped front face. Reducing the wall thickness in the tip region 207 allows this region to selectively expand when air is introduced while the reduced wall thickness in the neck region 206 facilitates removal of the balloon 200 from its mold.

While not explicitly illustrated, additional local variations in wall thickness can be implemented to achieve additional specific behavioral and performance characteristics in the balloon 200. Also not shown is a small flange that projects outward from the periphery of the side wall 202. This flange adds stiffness to the side wall 202, serves as a grip point when used with particular embodiments of an interface element 102, and provides a fluid seal in an embodiment of the present invention wherein a reagent is added to the multifunctional container 103 after cell collection has been completed.

Figure 9:
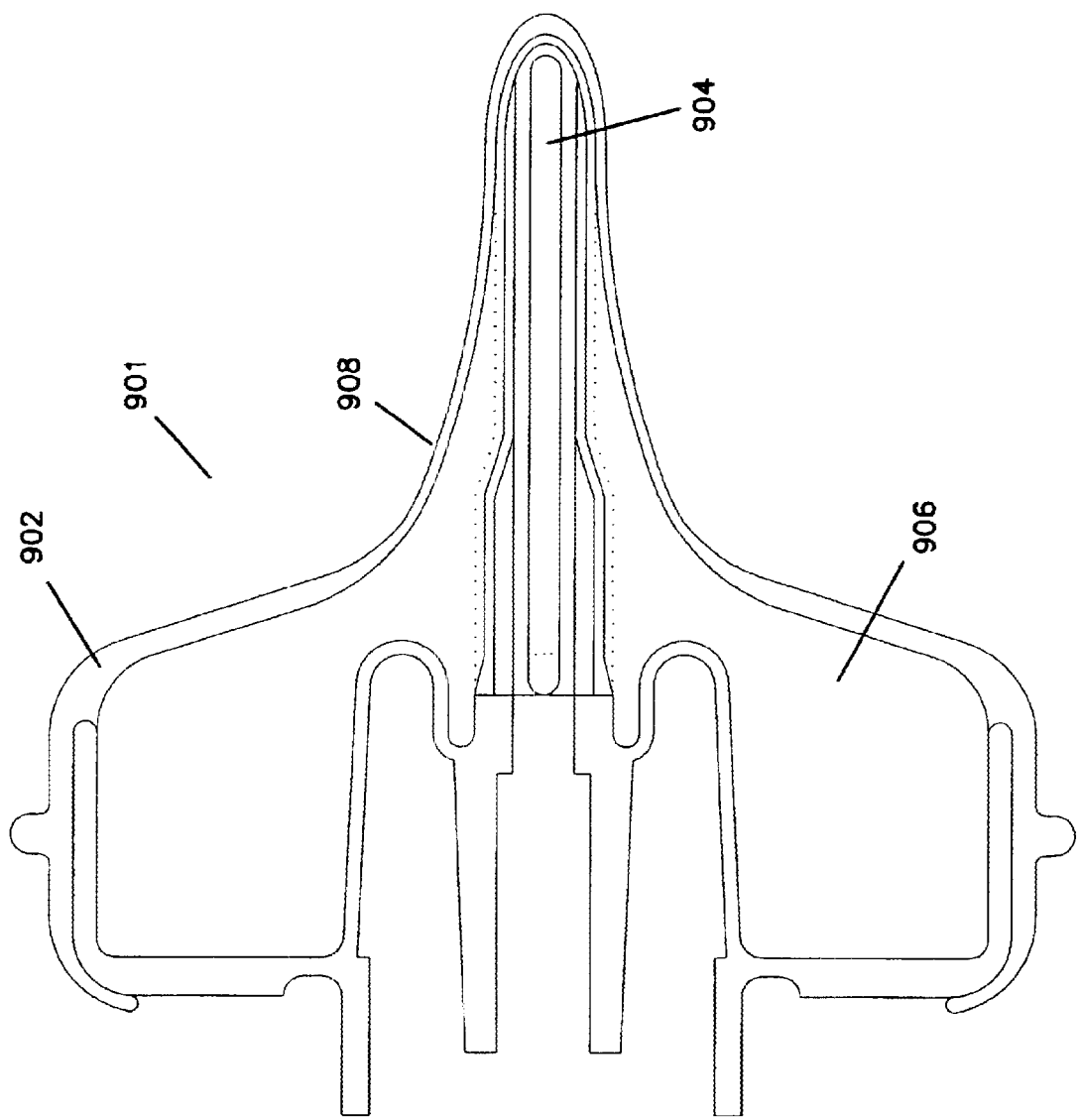
FIG. 9 is a sectional view of another embodiment of the sampling member in accordance with the present invention.

In another embodiment, the balloon 200 can include both an inner portion and an outer portion, as illustrated in FIG. 9. This Figure shows a balloon 901 that has both an inner balloon 906 and an outer balloon 902, as well as a stylette 904. It has been found that this particular embodiment can, in certain circumstances, provide additional control over inflation and deflation, as well as better control over the shape and configuration of the sampling surface 908. In one embodiment, only the inner balloon 906 is inflated or deflated, while in another embodiment, both inner and outer balloons 906 and 902, respectively, can be inflated or deflated either in combination or separately.

When the container 103 is released from the interface element 102, it can be slid to the opposite end of the handle 301 where it is retained in position by mating latching features 401. These are illustrated schematically as a quarter turn right-hand threaded male-female fastener pair, although other retention means such as snap latches can be employed for this function. These mating latching features 401 are configured such that once the container 103 is secured to the handle 301, the container 103 assumes a predefined rotational orientation with respect to the folded sampling member 101. The container 103, when secured at the end of the handle 301, forms a finger grip that can be held by the clinician. Preferably, the modified diamond shape of the end section of the container 103 is such that when naturally gripped by either a right or left handed clinician, the folded sampling member will assume a predefined rotational orientation with respect to the cervix into which it is to be inserted. Alignment marks, not shown, on the container 103 and handle 301 further encourage and guide the clinician to present the device to the cervix in this orientation.

As suggested by FIGS. 5A–5D, the clinician guides the device through a speculum into the vagina and inserts the tip of the sampling member 101 into the cervical canal 501 until the shoulder of the sampling member 101 seats against the cervix. See FIG. 5A. The flattened shape of the sampling member affords the clinician improved visibility of the cervix during insertion, while the bullet shaped tip of the sampling member and the stiffness imparted by the stylette 104 facilitate insertion of the sampling member 101 into the cervical canal 501.

Preferably, the stylette 104 is constructed of a compliant material such as low density polyethylene in a tubular form that provides adequate stiffness to aid in the insertion, but which can flex to avoid injury to the patient should the tip be misaligned with the cervical canal or should excessive force be applied during insertion. The stylette 104 can be a rigid floating member. The tubular nature of the stylette 104 also provides a means for introducing air into the sampling member 101 during the sampling process.

Figure 5A:
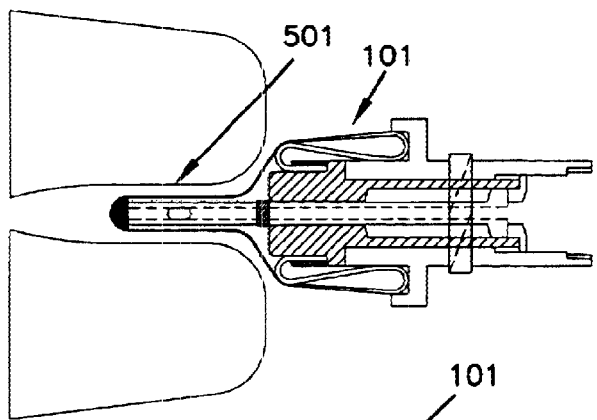
FIGS. 5A–D are sectional views of the physician's collector of FIG. 1, illustrating the use of the physician's collector in sampling cervical cells.
Figure 5B:
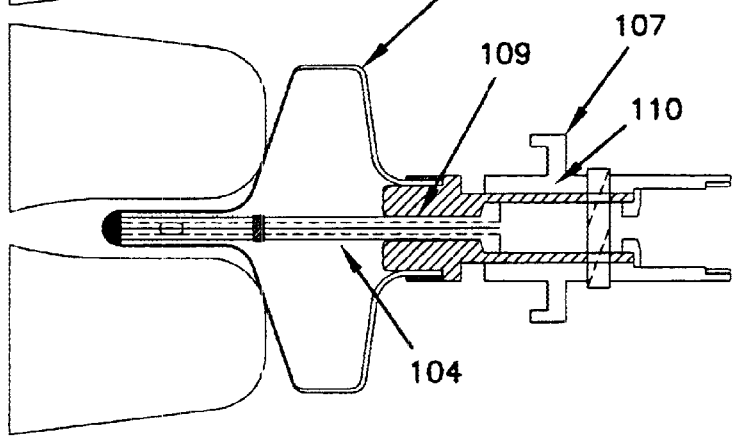

Insertion of the tip of the sampling member 101 into the cervix proceeds until the body of the sampling member 101 is properly seated against the mouth of the cervix, the sampling member 101 is deployed from its initial folded state into its unfolded sampling configuration as is shown in FIG. 5B.

Deployment is triggered partially by depressing the actuator button 303 at the end of the handle 301. The internal structure of the handle 301 can, in essence, be described as a syringe, the major elements of which consist of a barrel 304 that slides within the handle 301, an extension of which forms the actuator button 303; and a plunger 305 having an elongated hollow shaft 306 that is slideably retained in the body of the handle 301 and which makes air tight sliding contact with the interior of the barrel 304.

Figure 3:
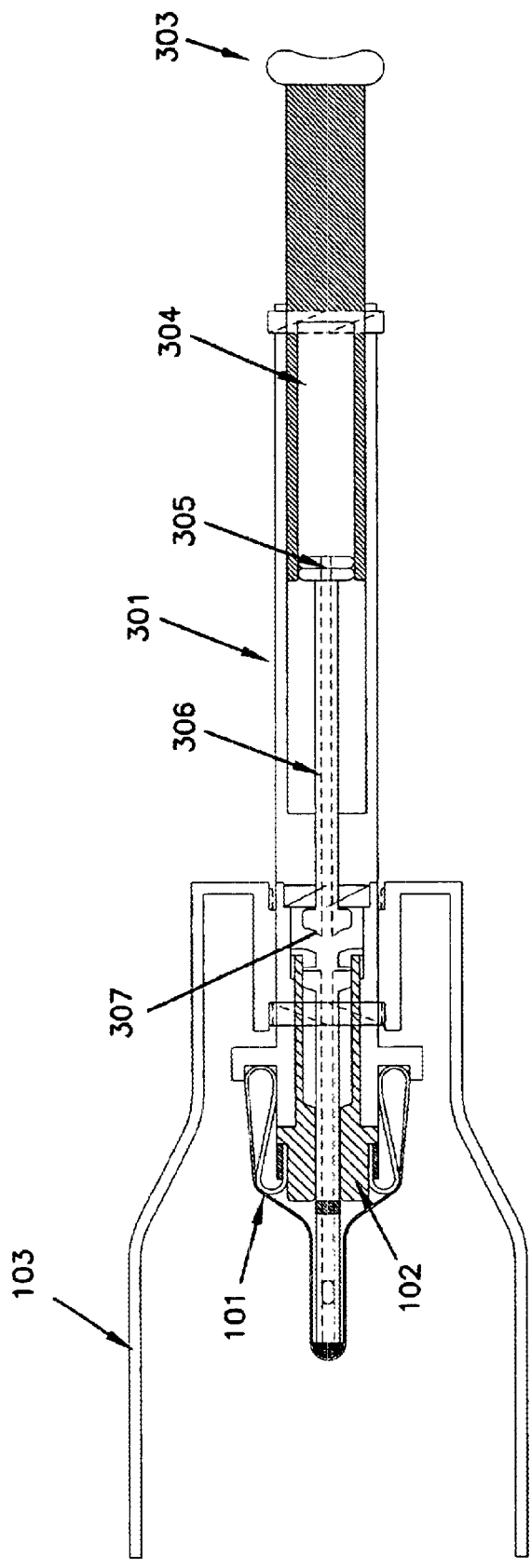
FIG. 3 is a sectional view of the physician's collector of FIG. 1, with a handle attached and a container positioned over the sampling member.
Figure 4:
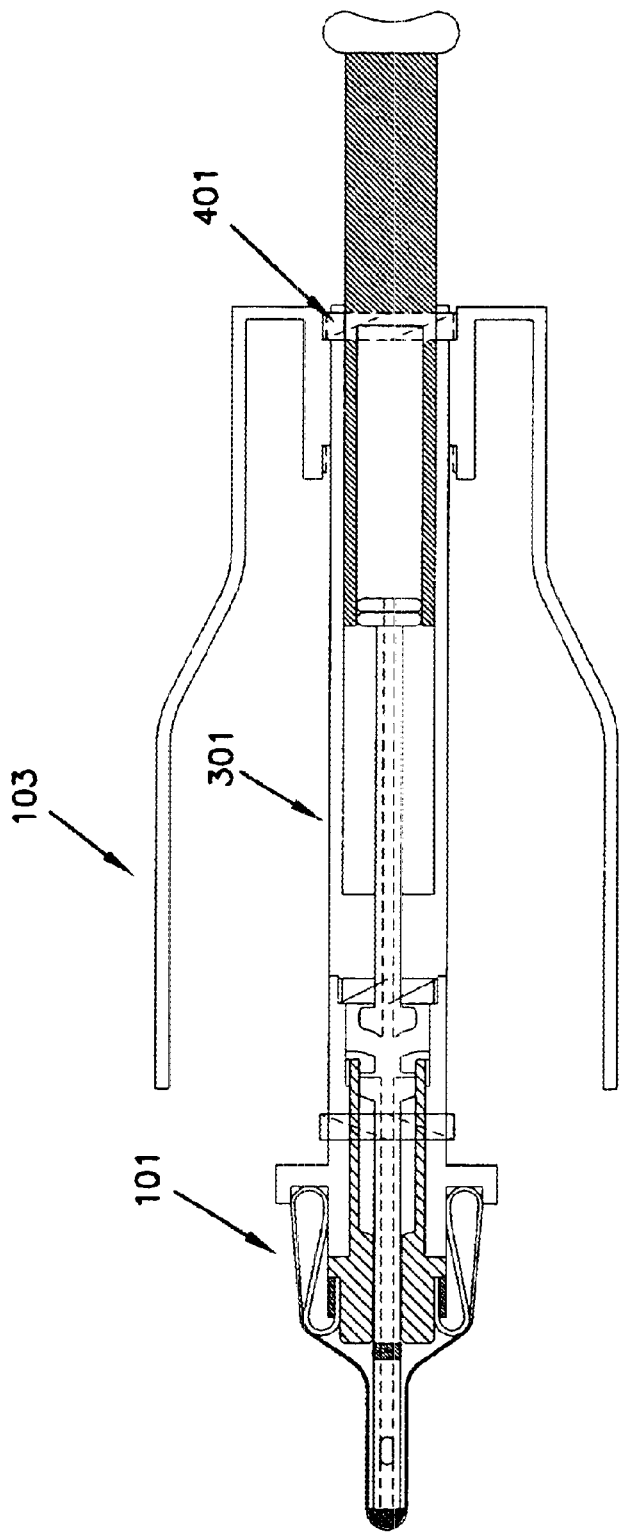
FIG. 4 is a sectional view of the physician's collector of FIG. 1, with the container positioned at the end of the handle.
Figure 5C:
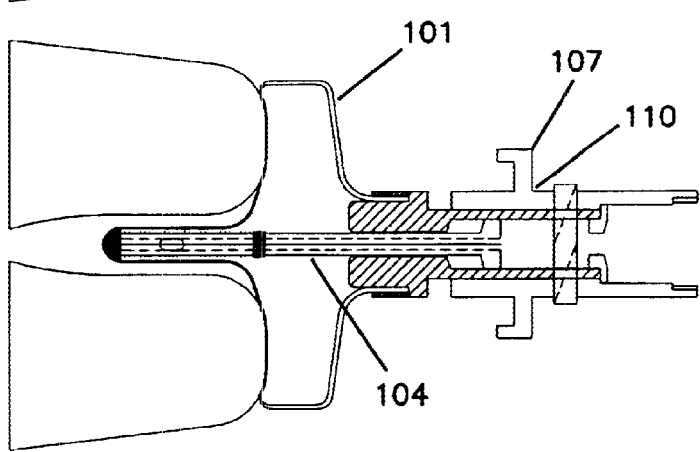

As the button 303 (FIG. 3) is initially depressed, friction between the plunger 305 and the barrel 304 causes the barrel 304, plunger 305 and hollow shaft 306 to move in unison in the direction of the sampling member 101 until the end 307 of the hollow shaft 306 makes contact with the inner portion of the interface element 102. Since the outer part of the interface element 109 is secured to the handle 301 by means of the latching features 107 and is thereby constrained from moving, continuing this motion forces the inner portion of the interface element 110 to move relative to the outer portion of the interface element 109 in the direction of the sampling member 101. This motion causes the sampling member 101 to move longitudinally with respect to the outer portion of the interface element 109 and thus to be released from the latching features 107 on the outer portion of the interface element 109. Once freed of the retaining features 107, the rear face 201 and side faces 202 of the sampling member 101 act as a spring that drives deployment of the sampling member into its unfolded state. Deployment ceases when the rear end of the stylette 104 seats against the inner surface of the inner portion of the interface element 109 forming an air tight seal. As is shown in FIG. 5C, pushing the handle toward the patient causes the side walls 202 of the sampling member 101 to move toward and ultimately to contact the surface thus draping the front wall of the sampling member 203 over the cervix. The sampling member 101 has a surface, when inflated, that approximates a endo-cervical region, as illustrated in the Figures.

The actions of inserting the tip of the sampling member into the cervical canal, deploying the sampling member and draping the front wall 203 (FIG. 5C) of the sampling member over the external cervix brings the cell collection surface of the device into substantial, but not necessarily complete, contact with those portions of the cervix from which samples are to be acquired. In particular, there are substantial variations in the shape and dimensions of the cervix and cervical canal between women which make it difficult to guarantee contact with all relevant areas when using a sampling device having fixed dimensions and shape. For this reason, the embodiment of the present invention being described utilizes selective expansion of portions of the sampling member to accommodate this range of human variability and to perfect contact between the device and the cervix to which it is applied.

This expansion is driven by the injection of air into the sampling member 101 and is controlled both by the wall thicknesses in the sampling member and by contact between the sampling member and the cervical tissue. Air is injected into the sampling member by means of the syringe structure incorporated into the handle 301. As noted earlier, the initial depression of the actuating button 303 on the handle 301 causes the barrel 304, plunger 305 and hollow shaft 306 to move in the direction of the sampling member 101 until the end of the hollow shaft 306 makes contact with the inner portion of the interface element 109. This contact causes the hollow shaft 306 to form an airtight seal with the interface element 109.

Figure 5D:
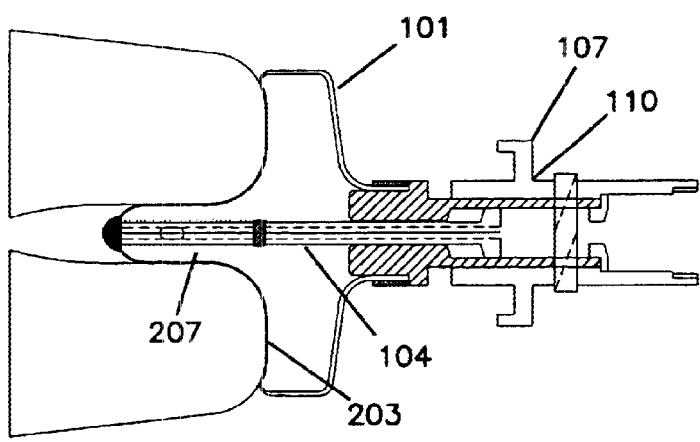

As the interface element 109 acts as a fixed stop against which the hollow shaft 306 presses, any further depression of the actuator button 303 will cause the barrel 304 of the syringe to move relative to the sealing element of the plunger 305. This relative motion causes air to be displaced through the hollow shaft 306, interface element 102 and stylette 104 into the sampling member 101 where it causes selective expansion of the front wall 203 and tip region 207 of the sampling member 101 in accordance with the constraints identified above and as is shown in FIG. 5D. As illustrated, the sampling member 101, when inflated, has a surface that is configured to approximate an endo-cervical portion of the cervix. The sampling member 101 can, when inflated, have a surface that is configured to approximate both the endo-cervical and the exo-cervical portions of the cervix.

Exfoliated cervical cells are transferred from the surface of the cervix to the surface of the sampling member 101 on contact between the surfaces. This transfer is facilitated by proper preparation of the cervix and by pre-conditioning of the sampling member. Mucus is generally present on the surface of the cervix and/or in the cervical canal. Similarly, blood and other fluids may also be present. As mucus, blood and other such extraneous materials can interfere with the evaluation of cervical samples, it is common practice to remove these extraneous materials from the cervix, typically by using a cotton swab, before a cellular sample is taken. This same convention is also practiced in conjunction with the present invention and results in a cervix that is relatively dry and free of extraneous materials.

Sampling by a contact means rather than by an abrading or scraping means as is employed by other cervical cell sampling devices confers certain benefits to the clinician. Cancerous lesions initiate at discrete foci and, except in extreme cases, are localized to specific regions of the cervix at the time of sampling. Contact sampling retains the spatial or topological relationships between the collected cells. Assuming that a lesion is present on the cervix, retention of the spatial relationships results in regions on the cell collection surface that are enriched in abnormal cells.

Localization of the abnormal cells on the surface of the cell collection device results in a higher signal to noise ratio between normal and abnormal cells, and thus improved detectability of abnormal cells relative to what is possible with samples obtained by an abrasive or scraping means where in the abnormal cells are dispersed throughout the sample.

Furthermore, localized sampling in conjunction with in-situ detection on the collection surface permit the locations on the cervix of any lesions detected to be presented to the clinician in a manner that directs the clinician to these specific areas of the cervix for the purposes of clinical follow-up. Detection of abnormalities in a sample obtained by abrasive or scraping means, on the other hand, requires that the clinician examine the entire cervix in order to determine the location of the lesion. Certain features of the present invention such as those that establish the orientation of the sampling member with respect to the cervix are particularly intended to support and facilitate use of the present invention in this manner.

Adhesion of exfoliated cells to the sampling member can be the result of the intrinsic properties of the materials used in the fabrication of the sampling member, or can be imparted to these materials by means of coatings or surface treatments. Many silicone rubbers, for example, exhibit an intrinsic tackiness that is capable of binding cells to the surface of the material. This is particularly true of low durometer formulations such as the GE 6030 materials available from General Electric, Waterford, N.Y. that have been cured to the minimum extent necessary to develop the required mechanical and physical properties. In addition, certain formulations of silicone rubber such as Shin Etsu 1935 available from Shincor, Akron, Ohio have been specifically formulated to have and to maintain a high level of surface tackiness.

The cell binding capability of a material can also be enhanced by surface modification or coating. For example, a variety of commercially available glow plasma or corona discharge and photochemical processes can be used to introduce charged species such as amino or carboxyl groups into the surface of the material. Such charged species are known to facilitate cell binding and, furthermore, can serve as "anchors" for the attachment of other cell binding materials to the surface. Glow discharge and photochemical processes can also be used to deposit coatings on most materials. The PhotoLink™ process offered by SurModics, Eden Prairie, Minn. is one of many such commercially available processes. Other coatings that enhance cell binding can be applied by a spray or dip process. For example, collagen fraction IV can be applied to silicone rubber from aqueous or acetic acid solution to enhance cell binding. The coating can include a silicone-based pressure sensitive adhesive.

Once the cellular sample has been collected on the surface of the sampling member 101 the device is removed from the patient. This is facilitated by releasing any air that may have been injected into the sampling member 101 during the sampling process. This can include applying a vacuum while removing the device from the patient. un the specific embodiment described here, release of the pressure being applied to the actuating button 303 allows the air pressure within the sampling member 101 to push on the syringe elements 304, 305, 306 within the handle 201 so that the entire syringe element moves away from the sampling element 101. This releases the mechanical pressure that maintains the air tight seal 601 between the hollow shaft of the plunger 306 and the interface element 109. Breaking these seals allows the escape of any air pressure within the sampling member that was not relieved by motion of the syringe element.

Figure 6A:
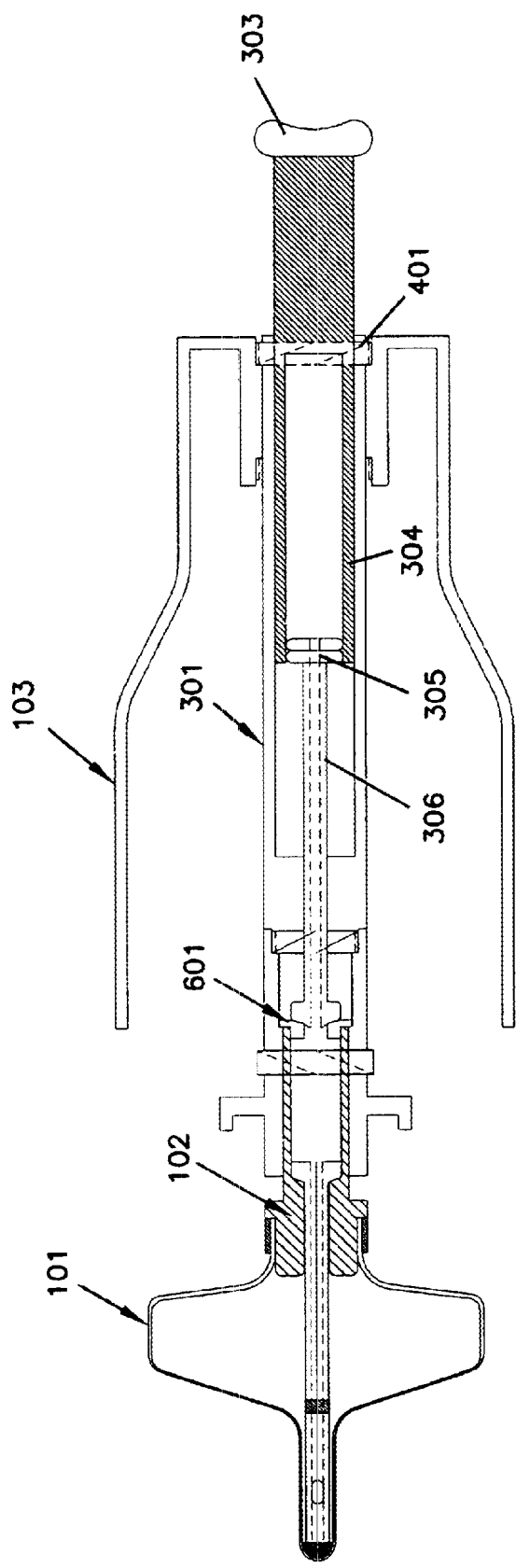
FIG. 6A is a sectional view of the physician's collector of FIG. 1, with the sampling member in an unfolded position. This corresponds to the configuration of the collector either immediately before or immediately after sample collection.
Figure 6B:
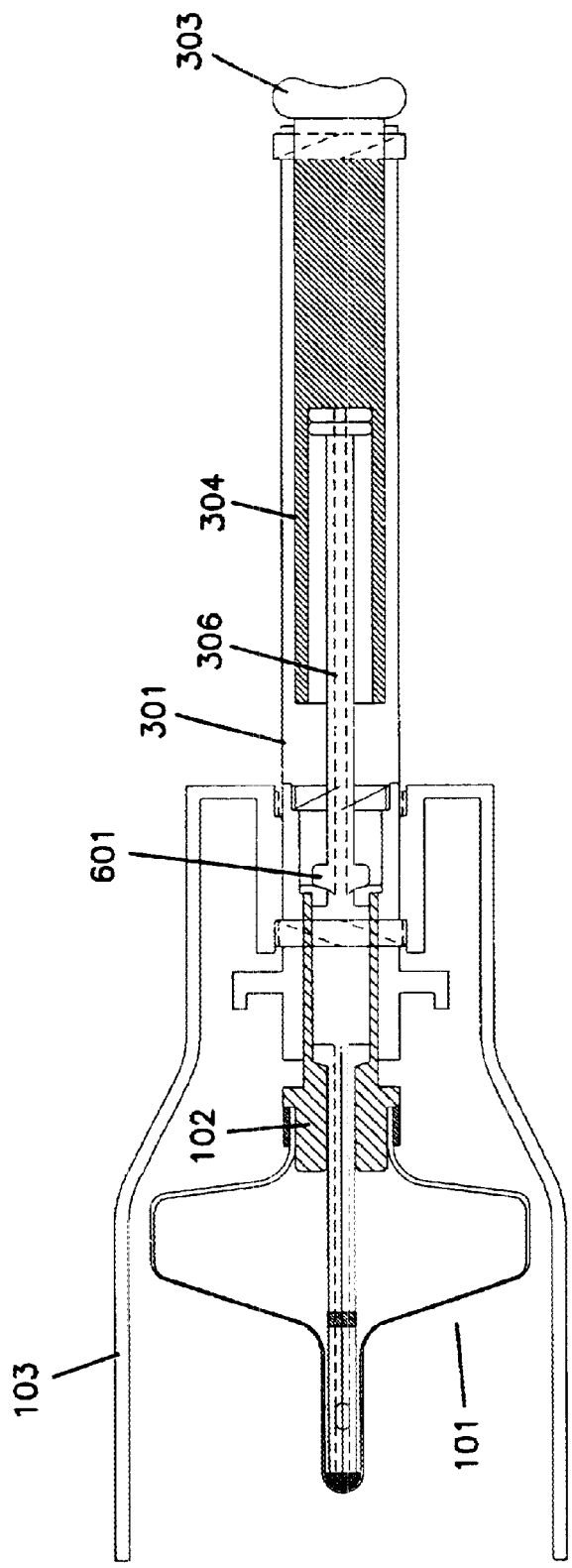
FIG. 6B is a sectional view of the physician's collector of FIG. 1, with the sampling member in an unfolded position, with the container secured over the sampling member. In this Figure, the handle has not yet been removed.

During removal of the device from the patient, the collected sample is protected from contact with the vaginal walls and other surfaces by the thickened rear 201 and side 202 walls of the sampling member. Once removed from the patient, the device is in the configuration depicted in FIG. 6A. The sample is protected by performing the reverse of the process previously described for exposing the sampling member. Specifically, the container 103 is released from the feature 401 retaining it to the handle; slid along the handle 301 until it encloses the sampling member 101; and secured to the interface element 102 by engaging the retaining features 108 between these two elements. The same motion that secures the container 103 to the interface element 102 releases the handle 301 from the interface element 102 and allows the handle 301 to be removed from the device. This places the device in the configuration shown in FIG. 6B. Using the handle 301 to guide movement of the container 103 relative to the sampling member 101 prevents the container 103 from coming into contact with the collected cells. This is in contrast to other cervical sampling devices wherein insertion of the device into a container is performed manually and thus may result in contact between the collected cells and the container.

Further protection of the collected sample is obtained by applying some form of closure to the open end of the container 103. Numerous forms of closure can be employed for this purpose. The simplest form of closure is a cap that can be applied to the open end of the container and preferably retained in position by friction, a snap feature or other similar means. The use of a simple cap, however, allows the possibility that the collected cellular sample may air dry and thus become unsuitable for evaluation.

Figure 7:
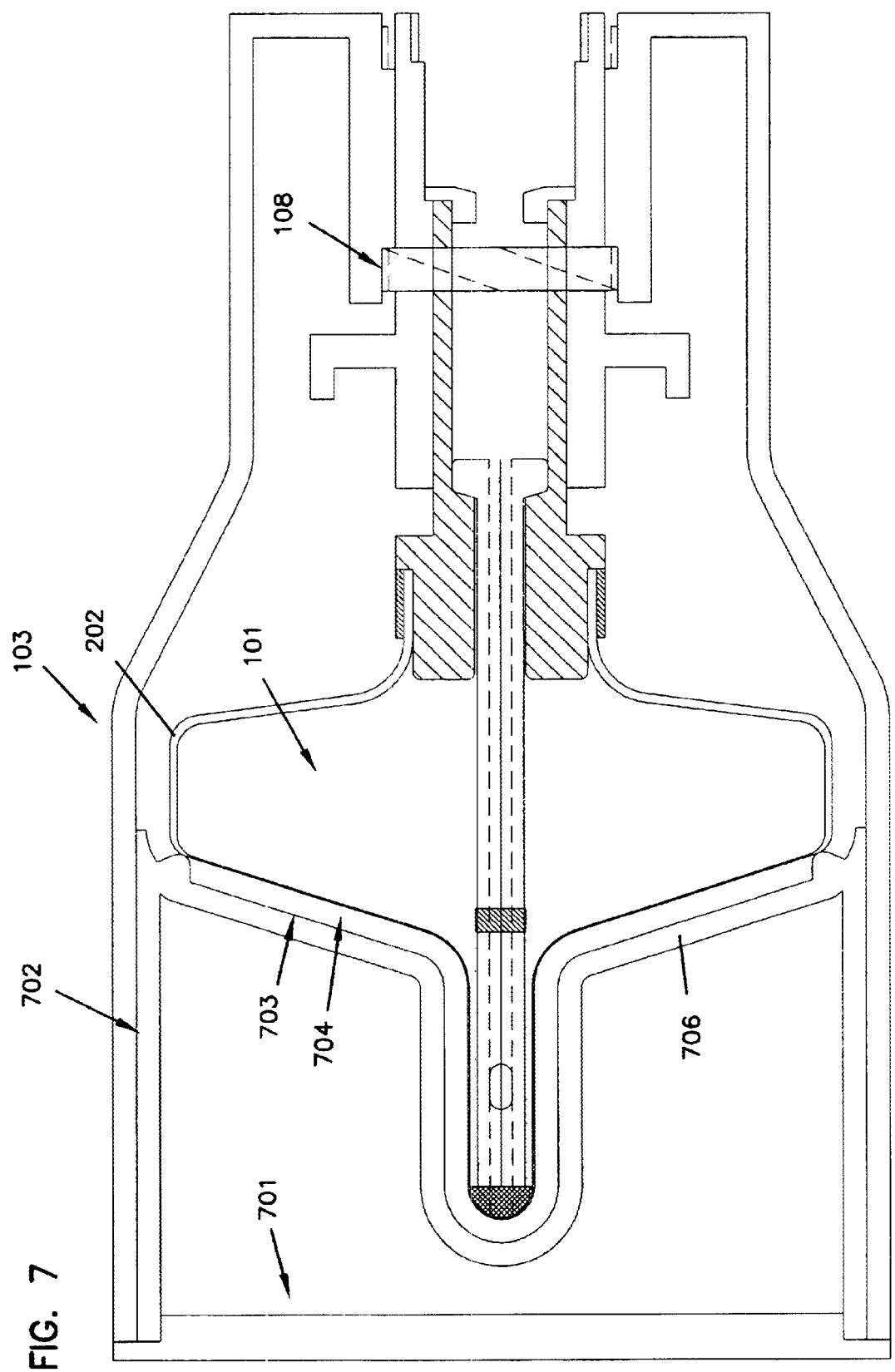
FIG. 7 is a sectional view of a plug element without fluid handling provisions.

A preferred closure means is shown in FIG. 7. This closure means takes the form of a plug 701 that incorporates a guiding surface 702 that allows the plug 701 to be inserted into the container 103 without coming into contact with the sampling member 101; threads or other means not detailed for securing the plug to the container; and a surface 703 that follows, but is spaced apart from the sample containing surface contacting either the side wall 202 of the sampling member 101 or a flange not shown protruding from this side wall to form a liquid tight compartment 704 that approximately conforms to the shape of the sampling surface of the sampling member. As the enclosed volume of this compartment is substantially less than the volume of a compartment formed by a simple cap, the potential for the sample becoming air dried is significantly reduced.

More complex plugs may be implemented depending upon the manner in which the collected cellular sample is to be processed and evaluated. In most instances, it is desirable to bring the cells into contact with a liquid medium at the earliest possible time after sample collection in order to eliminate the potential for air drying and to begin the processing of the cells. A suitable plug for this instance is as is shown in FIG. 7 and described above with the addition of one or more ports 706 through which the liquid medium can be injected or otherwise introduced into and/or removed from the liquid tight compartment 704. These ports may be configured such that the fluid medium can be introduced from an external source. Alternatively, the fluid medium can be incorporated into the body of the plug.

Figure 8:
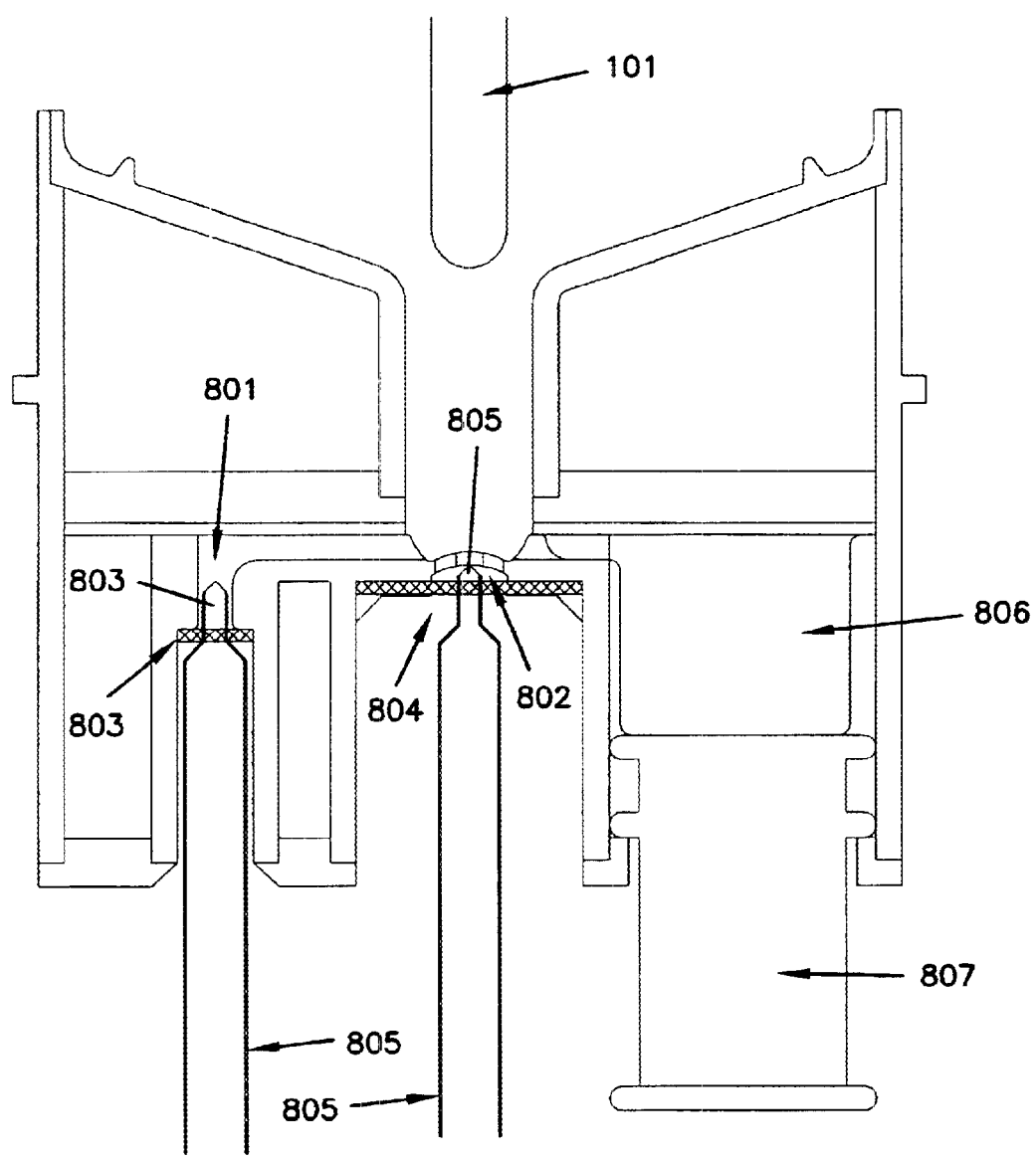
FIG. 8 is a sectional view of a plug element that incorporates fluid handling provisions as well as an internal reagent container.

An alternate embodiment of such a plug is shown in FIG. 8. This particular embodiment incorporates two externally accessible ports 801, 802 plus a compartment for a liquid medium contained within the plug body. One of the externally accessible ports 801 is intended for the introduction of an externally supplied fluid medium into the liquid tight compartment 704 while the second externally accessible port 802 is intended for the removal of the fluid from the compartment. Both ports are isolated by a sealing means shown schematically as septa 803, 804 in FIG. 8 to prevent unwanted fluid loss through these ports. This ports may be entered by probes 805 that communicate with the appropriate external fluidics. The internally contained fluid medium may be contained within a compartment within the plug not shown or within a secondary container 806 within such a compartment. The embodiment shown illustrates this secondary container as a flexible break seal pouch. Fluid is delivered from this pouch 806 into the liquid tight compartment 704 when an externally accessible plunger 807 is actuated. Although not explicitly shown in FIG. 8, the air displaced during the introduction of fluid into the fluid tight compartment is vented externally or into a compartment of the plug through holes in the wall of the plug or by air pressure displacement of the seal between the plug and the sampling member. Numerous other embodiments of these functions can be envisioned within the spirit of the present invention.

One anticipated manner of processing and evaluation is to remove the cells from the surface of the sampling member into a liquid suspension; deposit the cells from this suspension onto a microscope slide; and stain and evaluate the resulting specimen in the same manner as a conventional liquid based preparation. One suitable plug for this method of use is illustrated in FIG. 8 less the port 801 for the external introduction of the fluid medium. The fluid medium employed in this application is a cell preservative solution such as is available from commercial sources such as Cytyc Boxborough, Mass. and Tripath Imaging, Burlington, N.C.

The precise manner of use of such a plug depends upon the manner of adhesion between the collected cells and the surface of the sampling member 101. In each instance, after the plug 701 has been introduced into and secured to the container 103, the clinician actuates the plunger 807 to dispense the preservative solution into the liquid tight compartment 704 where it contacts the cells adhering to the collection surface. Certain coatings such as collagen fraction IV that may be applied to the sampling member to promote adhesion of the cells to the sampling member lose their ability to retain cells when immersed in an excess volume of a fluid medium such as the cell preservative solution. In this instance, static contact between the cell preservative solution and the surface of the sampling member is adequate to cause release of the collected cells into the fluid medium. In other instances, mechanical stimulation by, for example, shaking of the device or introduction of pulsating air pressure into the sampling member through the interface element, may be necessary in order to release the cells into suspension. In either case, the fluid medium containing the suspended cells is removed from the fluid tight compartment 704 by means of a port 802 and processed as a liquid based preparation by commercially available means such as those available from Cytyc, Boxborough, Mass., Tripath Imaging, Burlington, N.C., Sakura Fine Teck, Torrance, Calif. and others.

Another anticipated mode of use is in conjunction with a device for the in-situ detection and evaluation of abnormal cells on the surface of the sampling member. The specific embodiment of a plug that is applicable to this mode of use depends upon the specifics of the staining chemistry utilized in the detection process and the partitioning of functions within the detection device. One possible configuration requires that the collected cells be fixed on the surface of the sampling member before staining; that the staining protocol requires the sequential application of two different reagents to the cells; and that the cells be washed between steps in the protocol to remove excess reagent. It is further assumed, for the purposes of this example, that the fixative and both staining reagents are to be contained in the plug while the wash solution is introduced from an external source and that all processing subsequent to the introduction of the fixative will be carried out by an automated instrument.

A plug that is suitable for this mode of use is similar to that shown in FIG. 8 except that the number of reagent pouches is increased from one to three. The actuator 807 is associated with the break seal pouch 806 containing the fixative solution is designed such that it can be manually actuated by the clinician. The actuators associated with the pouches containing the staining reagents are similar to that associated with the fixative pouch except that the external protuberance has been removed. The result of this modification is that the pouches containing the staining reagents can be actuated by the processing instrument, but cannot be actuated manually.

After collection of the cells and after the plug 701 has been introduced into and secured to the container 103, the clinician actuates the plunger 807 to dispense the fixative solution into the liquid tight compartment 704 where it contacts the cells adhering to the collection surface. The entire assembly is then introduced into the processing instrument where the remaining steps of the protocol and the detection of abnormal cells are performed.

The fixative solution must remain in contact with the cells for a specified minimum period of time in order to ensure that the cells are properly conditioned for staining and that the cells remain adhered to the sampling member during processing. An instrument readable timer not shown is incorporated into the plug in order to ensure that this minimum time constraint has been met prior to the initiation of staining. This time can take the form of a fibrous body having defined and controlled fluid flow characteristics that is disposed in the wall of the plug such that one end of the fibrous body is exposed to the fluid in the fluid tight compartment while the other end is exposed in such a manner that its condition can be detected by the external instrument. Suitable fibrous bodies are available from numerous commercial sources such as Filtrona Richmond Richmond, Va.

In one embodiment of such a timer, a band of a colored or fluorescent material that is soluble in the fixative solution is applied to the fibrous body at a some distance from one end. In an alternative embodiment, a colorless or non-fluorescent material that reacts with the fixative solution to form a colored or fluorescent product is applied to the end of the fibrous body that is accessible to the external instrument. Contact of the fixative solution with the end of the fibrous body causes the fixative solution to wick along the length of the body at a controlled rate. The fluid flow properties and length of the body are selected such that the time required for the fluid front to traverse the distance between the ends of the fibrous body equals or exceeds the minimum acceptable fixation time. In the first described embodiment, the fluid front carries with it the colored or fluorescent material while, in the second embodiment, the colored or fluorescent material is formed in-situ by reaction of the fixative solution and the applied material precursor. In either case, arrival of the fluid front at the end of the body is indicated by an externally detectable change in the characteristics of the end of the fibrous body. The instrument delays initiation of the staining sequence until such a change is detected, thus ensuring that the minimum fixation time constraint has been satisfied.

The entire container-plug-sampling member assembly is oriented in the processing instrument with the plug end down. The instrument furthermore incorporates means to separate the plug 701 from the container 103 and to attach to and manipulate the sampling member 101 via the interface element 102. Processing is initiated by elevating the sampling member from its resting position relative to the plug and allowing the fixative to drain into the plug from which it is removed via the drain port 802. Wash solution is then introduced from an external source via the external fill port 801 into the well formed by the face of the plug. Note that the instrument may also introduce reagents into this well by means of a pipetting mechanism. The sampling member is lowered into the pool of wash solution and appropriately agitated to promote mixing and uniform washing. At the end of the wash period, the sampling member is raised above the pool and the wash solution is drained from the well as before. This cycle is repeated for each of the reagent addition steps in the staining protocol. At the end of the protocol, the processed sampling member is raised above the pool and dried prior to the detection process. The sampling member can be inflated prior to the detection process.

After detection is complete, the plug, container and sampling member are reassembled by the instrument and delivered to the user for disposal or further processing. This further processing can take the form of treating the cells adhering to the sampling membrane with a Pap or other stain that allows visual evaluation of the cells in-situ on the sampling member, or alternatively to release the cells into suspension for further evaluation as a liquid based preparation according to procedures that are analogous to those described previously.

Figure 11:
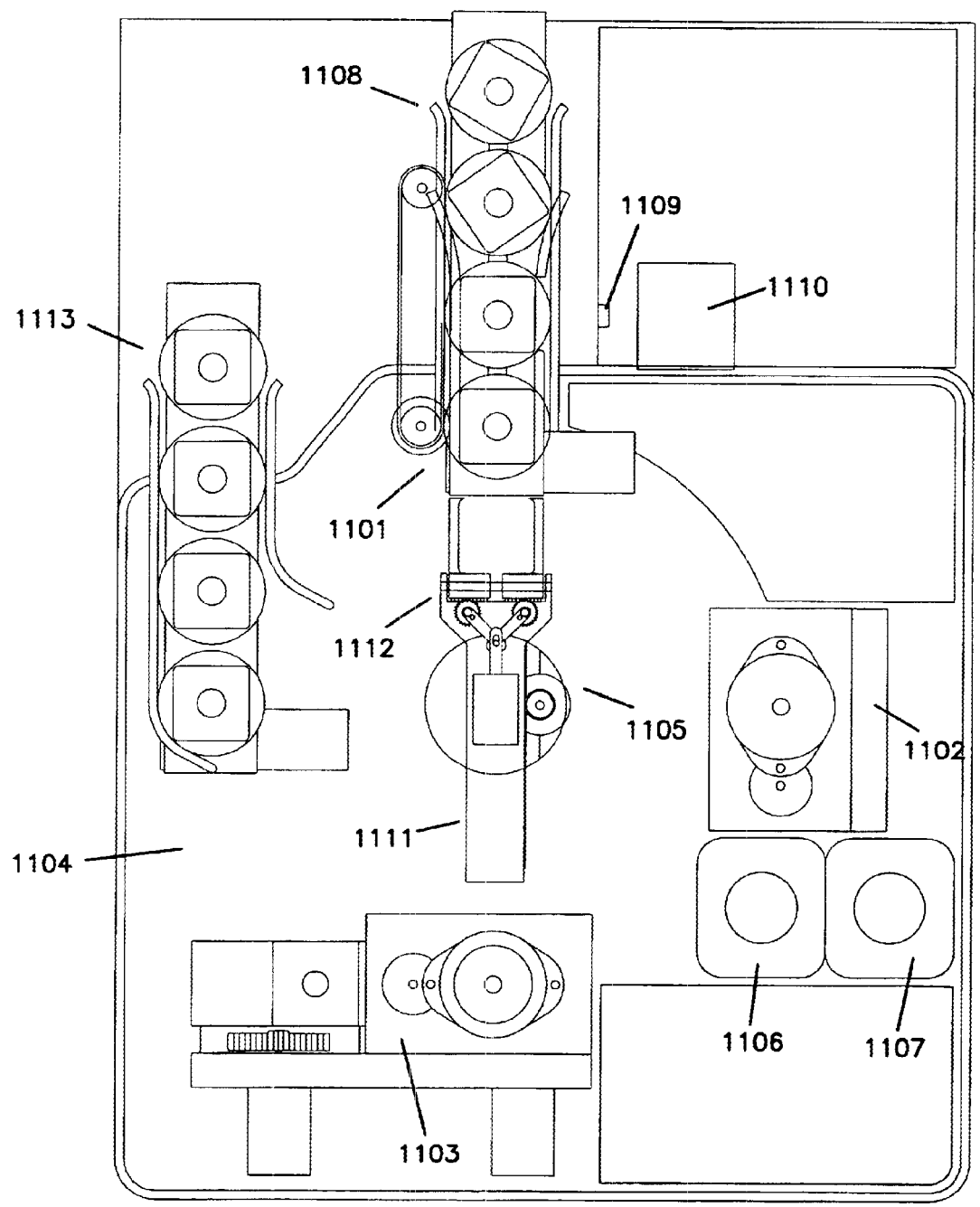
FIG. 11 is a plan view of an analysis instrument in accordance with the present invention.

An analysis instrument in accordance with the present invention is illustrated schematically in FIG. 11. The particular embodiment described below implements a cell staining protocol that is based upon the use of a primary antibody to which a fluorophore has been conjugated. The cellular sample is delivered to the instrument contained within the sample collection device 1000. A cell fixative solution within the sample collection device preserves the cells and preconditions them for staining. Upon transfer from the loading station 1101 to the processing station 1102 of the instrument, the fixative can be drained from the cell collection device 1000 into a waste container 1107 and the residual fixative is removed by exposing the cells on the supporting surface of the cell collection device 1000 to a wash solution that is provided from an external bulk container 1106.

The immunohistochemical fluorescent staining reagent is then applied to the cells from a compartment 1007 located within the closure element 1004 of the sample collection device 1000. After the staining reaction is completed, the used staining reagent can be drained from the reaction chamber, the adhered cells can be washed as before to remove residual staining reagent, and the stained cells can be dried on the surface of the cell collection element 1001. The cell collection element 1001 with adhering stained cells can then be transferred to a reading station 1103 where the locations and fluorescent intensities of any fluorescent objects on the surface of the cell collection element 1001 are determined in a spatially resolved manner. The acquired spatially resolved fluorescence data can be analyzed and the results of the analysis reported in graphical and/or numerical format as specified by the user. Processed cellular sampling devices can be delivered to the user for disposal or secondary processing.

One skilled in the art can readily discern means to extend, enhance and adapt the embodiment described. For example, although the embodiment described utilizes both unit dose and bulk reagent delivery methods, all reagents could be delivered in either unit dose or bulk form depending upon the needs of the present application. Similarly, although a single step fluorescent immunohistochemical staining protocol using a labeled primary antibody is described, protocols utilizing primary, secondary and higher level antibodies, avidin-biotin binding technology, DNA probes, enzymatic signal amplification and similar staining procedures can be implemented. The present invention is also not limited solely to fluorescent immunohistochemical staining procedures. Chromatic histochemical staining procedures can, for example, also be employed. Alternatively, the intrinsic auto fluorescence of cellular materials may be used for the classification of these samples. These and other enhancements, extensions and adaptations, either individually or in combination, lie within the spirit and scope of the present invention.

As shown in FIG. 11, samples are introduced into the instrument via a loading station 1101. The loading station 1101 provides a point where multiple samples can be queued for entry into the instrument and serves as a barrier that isolates the processing section of the instrument from external influences. Other functions can also be performed by the loading station to prepare the sample for processing, and to provide a measure of protection against certain types of operational faults and errors.

The queuing function of the loading station serves two primary purposes. One of these purposes is that it decouples operator intervention from the timing cycle of the sample processing. In the absence of a queue, the operator may only introduce a new sample into the system at those times during the processing of the previous sample when a position at the processing station 1102 is available. A queue, however, allows new samples to be introduced at any time subject only to the limitation of queue capacity.

The second purpose of the queuing function is to allow for the preconditioning of the samples before they enter the processing section of the instrument. Environmental parameters such as the temperature at which the staining reaction is performed have a substantial effect upon the time required to perform the staining, the degree of staining obtained and, in some cases, the ability of the stain to discriminate between various cellular constituents. To ensure consistency in the processing of samples, and thus to ensure that the results obtained from the processed samples can be compared on a common basis, those environmental parameters that affect the processing results must be controlled within suitable limits.

For example, the temperature within the processing section 1104 of the instrument is controlled within the range of 35±0.5° C. even though the operating temperature range outside of the processing section may vary between 15° C. and 30° C. Introducing samples, reagents and other materials at the external ambient temperature into processing section 1104 causes thermal transients within the processing section that should be eliminated or minimized before processing is initiated. Preconditioning the samples and reagents at a temperature that approximates the desired operating point minimizes the magnitude of the transient and, therefore, the time in processing section 1104 required to bring the temperature to within the desired limits. To this end, the loading station 101 incorporates a standard heating element and blower (not shown) that bathes the samples waiting in the queue with warmed air at a temperature that is approximately equal to the desired operating point temperature. When these prewarmed samples enter the processing area, only minor temperature adjustments are required to bring them to the desired operating point.

Similarly, the loading station 1101 serves to isolate or buffer the processing section 1104 from the external environment because the processing section can be completely enclosed except for a small port through which samples are transferred. A door, hatch or load lock mechanism of known design can be used to close the transfer port when samples are not being transferred should this added degree of isolation be preferred in a particular application. The loading station 1101 eliminates the need for a user to directly access the processing section 1104 and therefore eliminates or reduces the environmental transients associated with such direct access.

The loading station 1101 also works to minimize the potential for operator error. Preventing direct operator access to the processing section 1004, for example, eliminates the possibility that the operator may interrupt the process flow at in inappropriate time or cause other disruptions to the process. The loading station 1101 also incorporates geometrical and other features 1108 that ensure that the sample has been properly oriented and configured for introduction into the system.

As was previously described, the fixative solution must remain in contact with the collected cells for at least a certain minimum period of time in order to ensure that the collected cells will be properly stained. This minimum fixation period depends upon multiple factors including, for example, the type of staining to be performed. By way of example, more extensive cell fixation and permeabilization are required for a sample being treated with a stain directed against a constituent of the cell nucleus than for a sample where the stain is being directed against an extracellular membrane constituent. Fixation may, in the latter case, be completed in a matter of seconds while, in the former case, adequate fixation and permeabilization may require tens of minutes. Certain embodiments of the cell collection device described herein incorporate a liquid-based timing mechanism (not shown) that undergoes a change in color and reflectivity when the sample has been exposed to the fixative for an adequate period of time. Sample transfer from the loading station 1101 to the processing section 1104 is conditional upon detection of this change by a reflectance sensor 1109 incorporated into the loading station 1101, thus ensuring that only adequately fixed samples are presented to the processing station 1102 for staining. Samples that do not exhibit this reflectance change within a specified period of time after entering the loading station are rejected by the system.

The sample container 1003 can incorporate known labeling (not shown) that can communicate certain information. This labeling can, by way of example, carry information in machine readable form such as a bar code concerning the patient identification as well as the type of test to be performed, the lot and serial numbers of the sampling device, and the expiration date of the sampling device. The loading station 1101 can incorporate a suitable means 1110, such as a bar code scan engine or an imaging device, for reading this information from the label.

Such information can be used in multiple ways. The patient identification and sampling device serial number, for example, provide a means of linking a particular patient to a particular sample, and to the report that results from the processing and analysis of that sample. Information pertaining to the type of test allows the system to adjust various operating parameters such as reaction times and reagent volumes to suit the test to be performed while the sampling device lot number can convey calibration information that is specific to the collection device and reagents that are being used. The expiration date permits the system to reject samples where the collection device has exceeded its expiration date and is therefore suspect.

A transfer mechanism 1105 of known design is employed to move the sample between stations in the instrument. In the embodiment being described, the same transfer mechanism is employed to move the sample between the various stations. If desired, multiple transfer mechanisms can be employed. However, the functions of the processing and reading stations can be integrated into a single station, thus obviating the need for a means of transferring a sample between them. The preferred embodiment for a specific instance of the invention depends upon the particular application environment in which the invention is to be used.

The illustrated embodiment, for example, is intended for use in an environment where relatively few samples are to be processed and throughput, as measured in samples processed and read per unit time, is not a major consideration. Such an environment can be found in the practice of a solo physician or small group of physicians. Conversely, a large group practice, a reference laboratory, or a public health screening program typically requires a high throughput. An embodiment of the present invention intended for use in such a high throughput environment will typically incorporate multiple processing stations and multiple transfer mechanisms. In the highest throughput environments, there may be multiple instances of each of the station types within a single instrument. Each configuration imposes different requirements and thus design constraints on the transfer mechanism(s).

In the present embodiment, there is a single instance of each station type and the corresponding transfer mechanism is as shown in FIG. 11. In this instance, the transfer mechanism 1105 takes the form of a single arm 1111 having an end effector 1112 that is capable of grasping and releasing the sample 1000, and which is capable of radial, rotational and altitudinal motions. In operation, the arm 1111 rotates about a central vertical axis until the arm 1111 is aligned with the sample 1000 to be transferred from the initial station. The arm 1111 then extends radially until the end effector 1112 contacts and grasps the sample 1000. Raising the arm vertically lifts the sample until it is no longer in contact with the station being addressed and the sample can be withdrawn from the station by retracting the arm 1111 in the radial direction. The sample 1000 is moved to the target station by rotating the arm 1111 about its central axis until the sample 1000 is aligned with the target station; extending the arm 1111 radially until the sample 1000 is properly positioned within the target station; lowering arm until the sample 1000 is in contact with the target station; releasing the sample 1000 from the end effector 1112; and retracting the arm 1111 in the radial direction.

Figure 10:
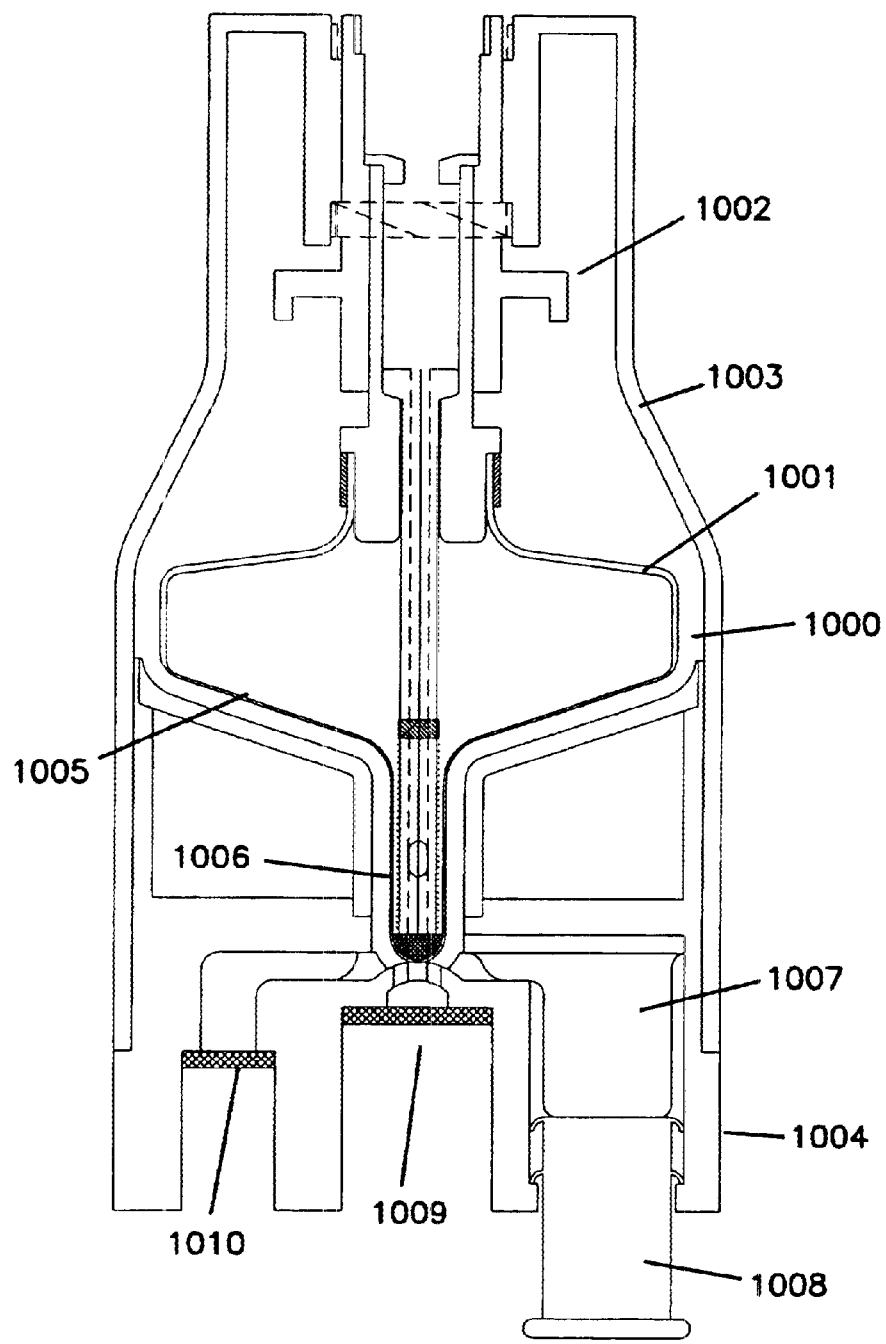
FIG. 10 is a sectional view of a cell collection device used in accordance with a preferred embodiment of the present invention.
Figure 12:
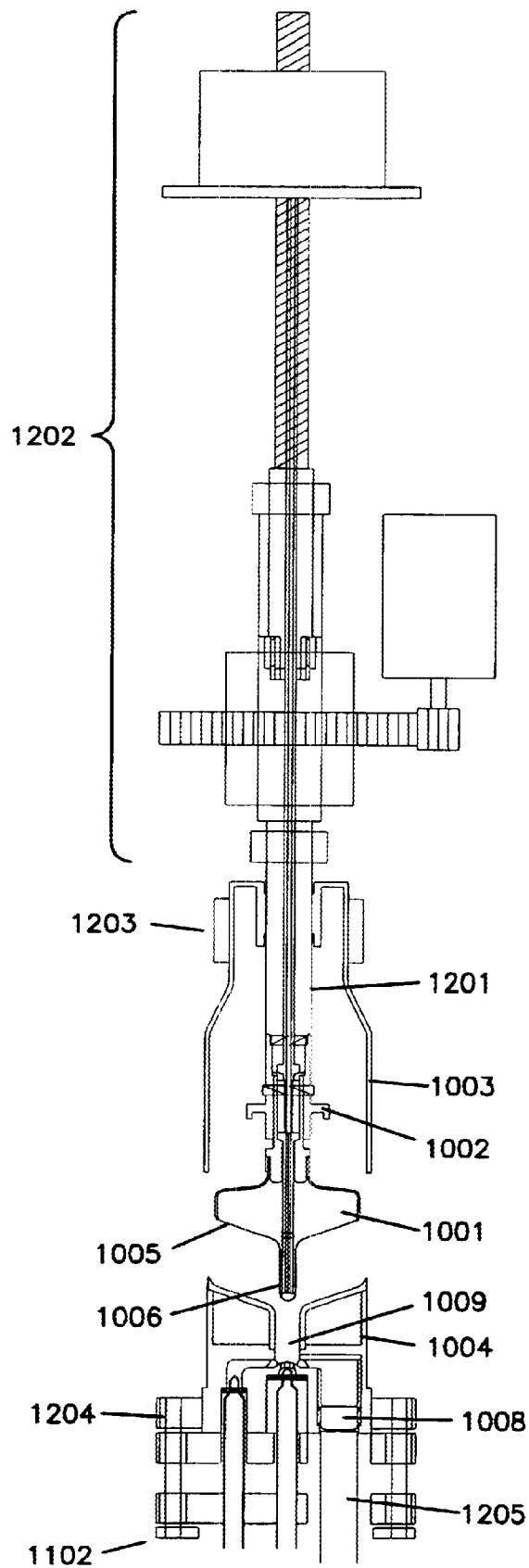
FIG. 12 is a sectional view of a sample processing station.

A preferred processing station is illustrated in FIGS. 10, 11 and 12. The sample 1000 is delivered to the processing station 1102 completely encased in a container that must be opened before the sample can be processed. The transfer mechanism 1105 delivers the sample collection device to the processing station 1102 in an orientation such that three access ports 1008, 1009 and 1010 in the end closure 1004 and the coupling element 1002 on the opposite face of the sample collection device are aligned with the corresponding features in the processing station. Additional features in the processing station mate with ridges and flats (not shown) incorporated into the outer surface of the sample collection device 1000 in a manner that allows clamp mechanisms 1203 and 1204 to secure the container 1003 and end closure 1004, respectively, to the processing station 1102.

When the collection device 1000 is properly positioned and is secured in the processing station 1102 by clamp 1204, a shaft 1201 is extended from the processing station 1102 and engages the coupling element 1002 on the collection device. Rotating shaft 1201 disengages the sampling element 1001 from the shell 1003 of the collection device 1000 and separates the shell 1003 from the end closure 1004. Slightly retracting shaft 1201 lifts the shell 1003 from the end closure 1004 to a position where the shell 1003 is secured in place by clamping mechanism 1203. This leaves the sampling element 1001 suspended above the end closure 1004, the face 1005 of which is contoured in a manner that mirrors the contour of the face of the sampling element 1001. The contoured face of the end closure 1004 forms a well into which reagents can be introduced and into which the sampling element can be dipped for the purpose of performing the staining and washing reactions.

At this point, the reaction well contains the fixative solution that was applied to the sample prior to introduction of the sample into the instrument. As illustrated in FIG. 10, this fixative is drained from the well through the central port 1009 in the end closure. The well is then filled with wash solution from the bulk supply via a second port 1010 in the end closure 1004 and the sampling element 1001 lowered until the face of the element is immersed in the wash solution. Washing can be facilitated by rotating or oscillating the sampling element longitudinally or, alternatively, by introducing a pulsating stream of air into the sampling element via a channel in the coupling element. Upon completion of the washing, the sampling element is raised above the well and the used wash solution is drained as before. The wash cycle may be repeated as needed until the excess fixative has been removed from the sampling element.

Upon completion of the removal of the fixative solution, the staining reagent is introduced into the reaction well. In the configuration illustrated, the reagent is contained in a break-seal pouch 1007 within the end closure 1004 of the sampling device 1000. As suggested in FIG. 12, the instrument extends a plunger 1205 through an access port 1008 in the end closure 1004 of the sampling device 1000 to compress the reagent pouch 1007. This pressure causes the break-seal to rupture, thus discharging the contents of the pouch into the reaction well. The staining reaction is carried out by immersing the sampling element into the pool of reagent in the reaction well and mixing as described above. At the conclusion of the staining reaction, the sampling element is elevated above the reaction chamber, the spent reagent is drained from the chamber, and the sampling element washed as described above. The washed sampling element can be dried in a stream of warm, dry air. Other dispensing means such as spraying, aspirating, nebulizing or pipetting may be employed to deliver fixative, staining reagents and wash solution to the sampling element 1001. Such alternative dispensing means will require that the design and operation of the process station 1102 will differ from that described above.

The preceding description assumes that the sampling element 1001 is positioned directly above the reaction chamber such that the entire face of the sampling element 1001 can be simultaneously immersed in the reagent pool. This arrangement is acceptable for many applications. However, in some applications the reagent(s) are expensive, in short supply, or, for other reasons, must be conserved. The volume of reagent required to process a sample can be reduced by tilting the sampling element 1001 away from the vertical and making corresponding changes in the shape of the face of the end closure (reaction well). In this configuration the well is filled only to a level that ensures at least a continuous line of contact between the reagent and the sampling element. Rotating the sampling element about its axis of symmetry causes the reagent to coat the entire surface of the sampling element. The optimum tilt angle to minimize the consumption of reagent is determined by the shape and dimensions of the sampling element. In the case of one particular type of sampling element, it was possible to reduce the volume of reagent required by approximately 60% by tilting the sampling element by 50 degrees away from the vertical.

The rate of drying of the sampling element is determined by the amount of residual fluid on the surface of the sampling element and by the volatility of this fluid. The drying rate can be increased by rinsing the sampling element in a water miscible, volatile cell fixative solution such as ethanol or isopropanol prior to drying.

Figure 13:
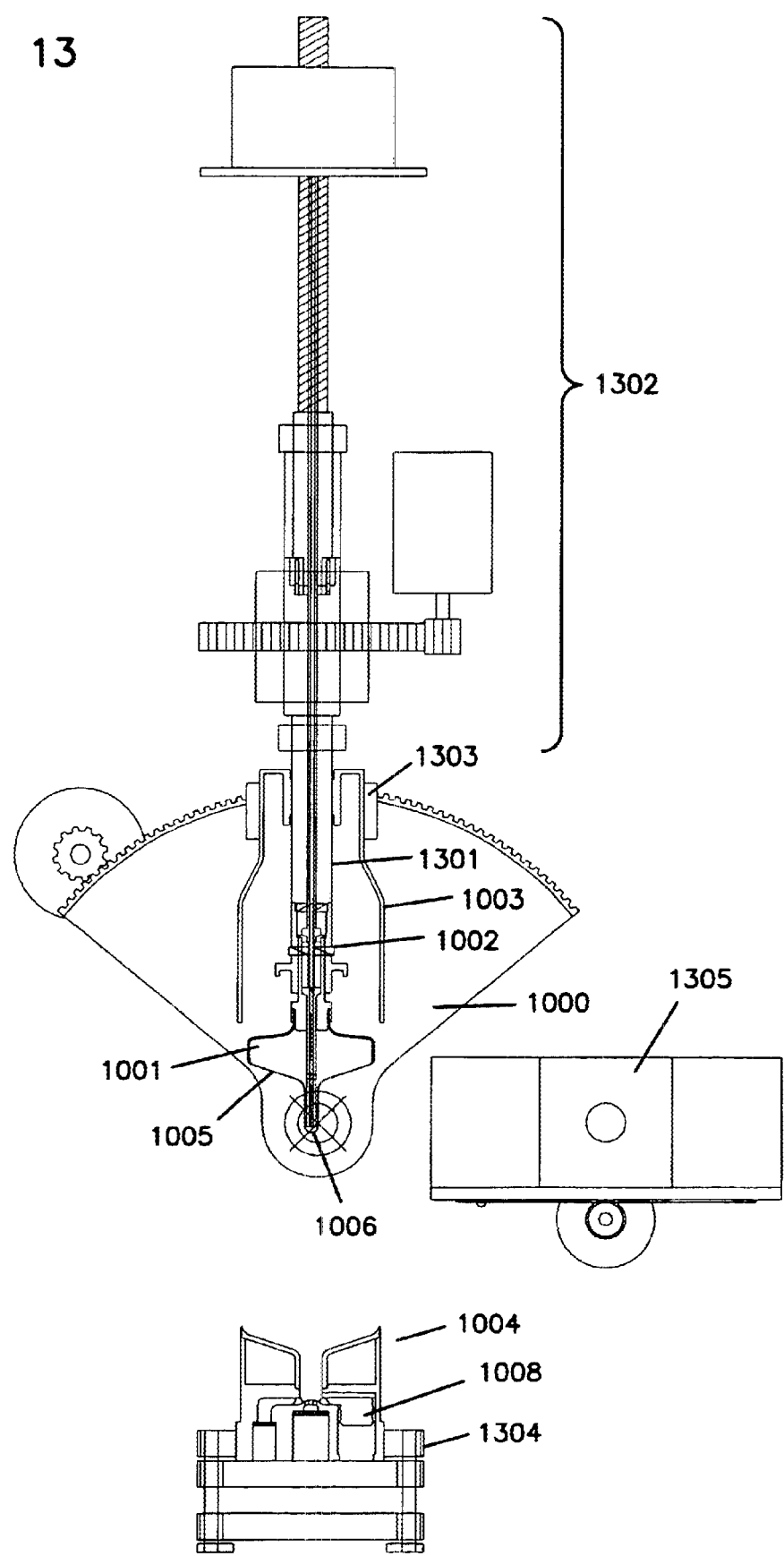
FIG. 13 is a sectional view of a reading station.

Upon completion of the staining, washing and drying, the sample container is reclosed, the sampling device 1000 is disconnected from the vertical shaft 1201, and the device 1000 is moved to the reading station 1103 by the transfer mechanism 1105. The reading station 1103 is illustrated more fully in FIG. 13. When the collection device 1000 is properly positioned and secured, by clamp 1304, in the reading station 1103 (FIG. 11), a shaft 1301 extends from the reading station 1103 and engages the coupling element 1002 on the collection device 1000. A rotating shaft 1301 disengages the sampling element 1001 from the shell 1003 of the collection device 1000 and separates the shell 1003 from the end closure 1004. The retracting shaft 1301 lifts the shell 1003 from the end closure 1004 to a position where the shell 1003 is secured in place by a clamping mechanism 1303. This suspends the sampling element 1001 a sufficient distance above the end closure 1004 to provide the reader optics 1305 with the necessary access to the stained cellular material on the surfaces 1005 and 1006 of the sampling element 1001.

The primary function of the reading station 1103 is to measure the fluorescence at each point on the surface of the face of the sampling element 1001. To this end, either of two optical systems are used depending upon whether, in the particular application, it is necessary or desirable for the operator to be able to visually view the surface of the sampling element. If, as is the case in research and certain other specialized applications, it is desirable for the operator to be able to visually view the surface of the sampling element, the optical system consists of a video camera or viewing tube coupled to an appropriate microscope objective lens.

Figure 14:
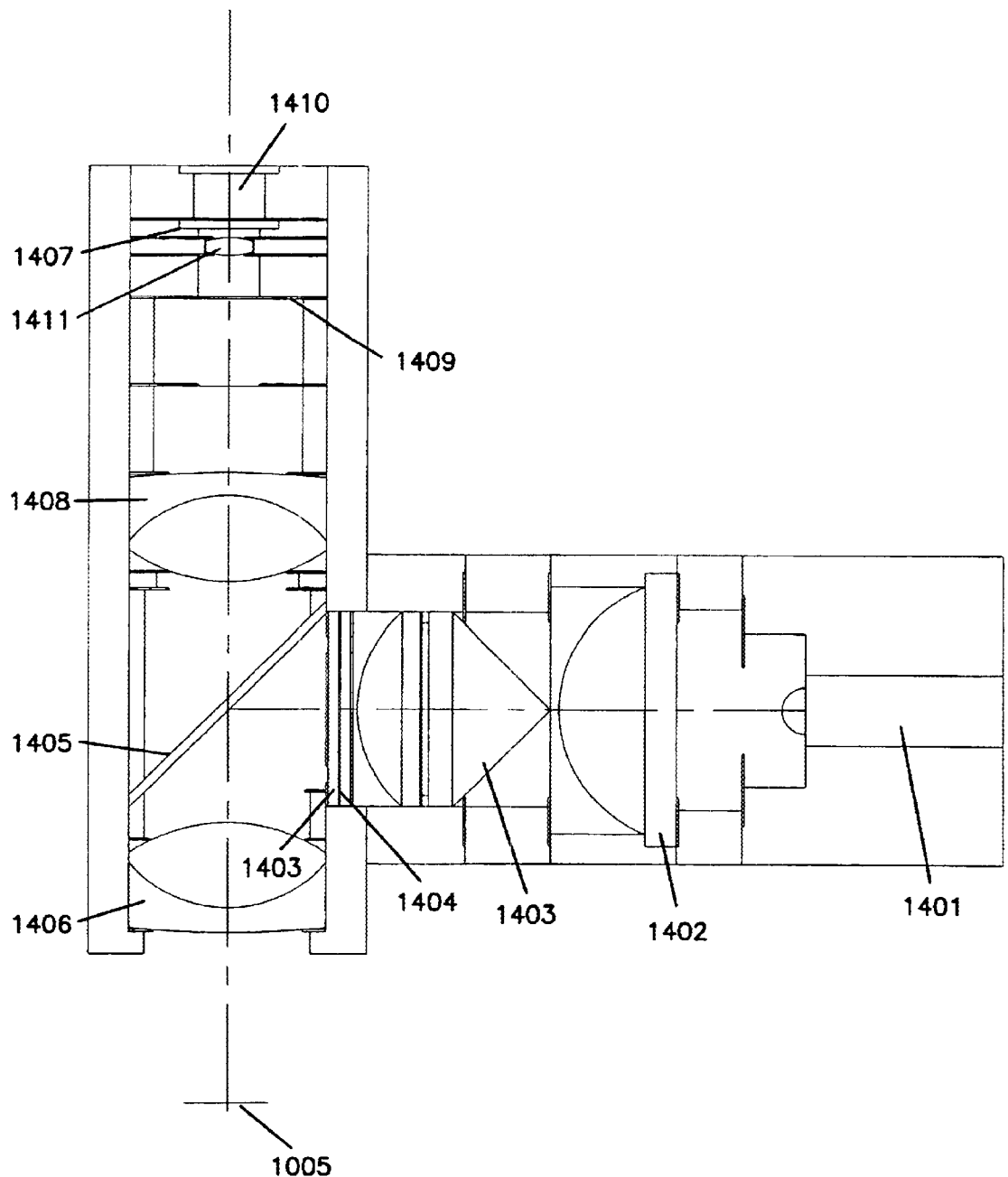
FIG. 14 is a sectional view of a optical system.

In applications where it is neither necessary nor desirable for the operator to view the surface, a flying spot scanning optical system is employed. The flying spot optical system shown in FIG. 14 is of a dark field, epi-illumination confocal design having approximately ten micron spatial resolution at the surface of the sampling element. Proper selection of the light source 1401 and wavelength selection filters 1404 and 1407 and dichroic mirror 1405 allows this optical system to be used with fluorescent immunohistochemical staining reagents incorporating any desired fluorophore. Other selections allow the use of nonfluorescent reagents such as standard histochemical stains.

In this design, light emitted from light source 1401 is collimated by a lens 1402 and converted to a collimated ring of light by an axicon 1404. Interference filters 1403 are used to select the excitation wavelength. A dichroic mirror 1405 redirects the illumination such that it is coaxial with the optical axis of the scanning optics. A high numeric aperture doublet lens 1406 used as an objective focuses the illumination on the surface 1005 of the sampling member 1001. The illumination incident on objective lens 1406 is in the form of a ring that passes through the periphery, but not the center of the lens. The relationship between the inner and outer diameters of this ring of light and the numerical aperture of the objective lens 1406 are selected to establish dark field illumination conditions where specular reflections from the surface of the sampling element do not reenter the central portion of the objective lens. This increases the signal to noise ratio in the detected signal and relaxes the performance requirements placed on the detection optics.

Fluorescent light emitted by the sample is collected and approximately collimated by the central portion of the objective lens 1406. This collected collimated light passes through the dichroic mirror 1405 and is focused by a second doublet lens 1408 that is identical to the objective lens 1406 upon pinhole aperture 1409 which defines the size of the sampling spot on the surface of the sampling element 1001. Light passing through aperture 1409 is collimated by collimating lens 1411 and the fluorescence emission wavelength to be detected is selected by interference filter 1407. Photodetector 1410 converts the incident light energy into an electrical signal. In some applications, it is desirable to replace filter 1407 with an optical subsystem that allows the simultaneous detection of emitted light at multiple wavelengths.

The shape, reproducibility and stability of the sampling element 1001 and the type of optical system determine the characteristics required of the positioning system that is employed in the reading station 1103. The function of the positioning system is to move sampling element 1001 in such a manner that the optical axis of the reader optics 1305 traces a prescribed path over the entire face 1005 and tip 1006 surface of sampling element 1001. In order to minimize measurement errors, the optical axis must be perpendicular to the surface of the sampling element 1001 at each point on said surface. Furthermore, the surface of the sampling element 1001 must remain within the depth of focus of the optical system throughout the scanning process. The resolution, accuracy and precision required of the positioning system is determined by the type of optical system employed. An optical system based upon a CCD video camera, for example, imposes less stringent demands upon accuracy, precision and resolution than does a flying spot scanner because, in the former case, the effects of several of the predominant types of positioning error can be compensated for during the processing of the acquired data. Similarly, the means (not shown) employed for determining the position and alignment of the optical system 1305 relative to the surface of sampling element 1001 depends upon the type of optical system employed. The embodiment illustrated in FIG. 13 utilizes two linear and two rotary axes of motion, all under servo control, to accomplish these ends. An alternative optical system that does not provide spatially resolved data, and thus does not require precise positioning of sampling element 1001 relative to the reader optics 1305, can also be envisioned.

The electrical signal produced by the photo detector 1410 is amplified, filtered and digitized by means not shown to produce a numerical representation of the distribution of fluorescence on the surface of the sampling element. This numerical data is processed to detect the presence of abnormal cells on the surface of the sampling element 1001 and to classify such abnormal cells as may be detected.

Known calibration standards and procedural controls may be incorporated into the system to ensure that the optical system and detection electronics have been properly adjusted and that the staining reaction has been performed successfully. A typical calibrator may consist of a material such as fluorescent microparticles having known characteristics that are disposed in such a manner, including but not limited to locations on the surface of the sampling element, that the material can be viewed and quantitated by the optical system. A typical procedural control may, by way of example, consist of a material that absorbs or reacts with the staining reagent in such a manner to give an optical signal of a predetermined level if the sample staining reaction has been properly performed.

After background correction and normalization, a histogram of the values of the collected data points is constructed and analyzed to determine the threshold data value that discriminates between normal and abnormal cells. This threshold value is constrained to ensure that the gradient search method used to locate the threshold value has converged on an acceptable value that is consistent with the values determined during the characterization of the staining reagent. The threshold is used to select those data points having signal levels that may indicate the presence of an abnormal cell.

The thresholded data is then processed to aggregate groups of data points that are in proximity to one another into "objects". The area of each object, defined as the number of data points included within the boundaries of the object, the average of the values of these data points, the ratio of the average data value to the area of the object, and other parameters are computed. As the optical system is designed such that each collected data element is smaller than the smallest abnormal cell of interest, the area of any detected object that may be a cell must be greater than a particular value that is determined during system calibration. Any object having an area that is smaller than this predetermined value is rejected as being non-cellular. Other morphological parameters such as the length to width ratio of an object may also be used in the discrimination between cellular and non-cellular materials. Characterization of the staining reagent establishes the range of average data values corresponding to abnormal cells.

Objects having average data values outside of this range are rejected as being non-cellular. The remaining objects are presumed to be abnormal cells that may, if desired, be further classified on the basis of object area, average data value and other parameters so as to indicate the degree of abnormality of the cell.

Some fluorescent immunohistochemical reagents do not, by themselves, provide sufficient discrimination between normal and abnormal cells, between cell types or between cellular and non cellular materials to meet accepted clinical standards. In these cases, multiple reagents each having different specificities and distinguishable fluorescent properties are applied to the sample and quantitated by the optical system. The reagents in such a combination may, for example, be directed against different antigenic determinants in the cells or an immunological reagent directed against a particular determinant may be combined with a reagent such as propidium iodide that discriminates between cellular and non-cellular materials. The data analysis process is extended to select and classify objects based upon measurements made of these combinations of fluorophores.

The results of the data analysis are reported to the clinician in a form that reflects the needs of the particular application. Samples taken as part of a screening program may, for example, be reported as being within normal limits if no abnormal cells are detected, or marked to indicate the presence of abnormal cells. In a diagnostic application, abnormal cells, may be reported in a manner that reflects the degree of abnormality detected. One typical report is a printout or visual display that lists the findings of the analysis and other desired information such as patient identification. The report may include the classification of each abnormal cell detected or it may provide a classification for the entire specimen based upon a composite of the classifications of the individual abnormal cells detected.

The sample collection and analysis process described above preserves the spatial relationships that existed between the cells before collection. In other words, cells collected from a lesion (a group of abnormal cells) will be clustered together on the surface of the sampling element. As the sampling, staining, and data analysis processes retain this spatial information and this spatial information can be linked to an absolute physical location on the sampling element in a manner that allows this location to be linked to a specific position on the cervix, the analytical results can be presented in the form of a map that displays the location of the detected abnormality on the cervix. The clinician can use this map to guide whatever confirmatory and follow-up procedures are indicated to the specific location(s) on the cervix where the abnormalities exist.

The cells processed using the present invention can be released from the surface of the sampling element and deposited on the surface of a conventional microscope slide using known liquid-based slide preparation techniques. These slides may then be used for the purposes of confirmation of results, additional testing or cytological diagnosis using other methods. The fluorescent immunohistochemical stains applied to the cells by the present invention are retained by the cells upon transfer to a microscope slide. Under certain conditions—specifically that subsequent staining processes do not suppress or mask the fluorescence of these stains—these fluorescently stained cells can be visualized by fluorescence microscopy. This fluorescence can guide the cytologist to specific regions of the slide where abnormal cells are present and may thus facilitate evaluation of the slide.

Figure 15:
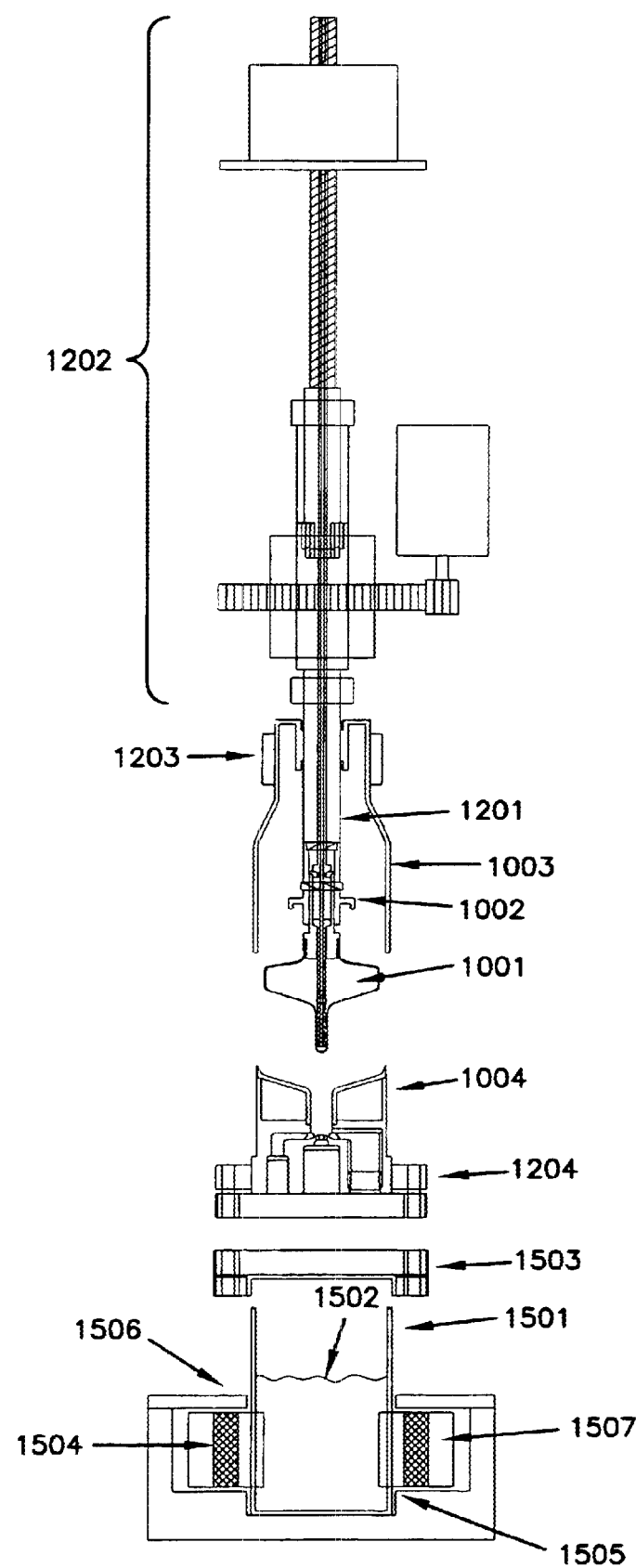
FIG. 15 is a sectional view of the cell collection device according to FIG. 10, illustrating an optional washing system.

In a preferred embodiment, the cells are removed using an apparatus as illustrated in FIG. 15. A user inserts a capped vial of preservative solution into a well 1506 in the base of the instrument and then inserts a sealed canister containing cells into a slot (not shown) in the housing face of the instrument that is located directly above the well for the preservative solution. A vial clamp 1507 secures the vial in the well.

A rotary decapping mechanism 1503 extends from the instrument over the vial; is lowered to make contact with the vial cap; grasps and unscrews the cap; raises the cap above the vial; and retracts the cap into the instrument. A plug removal mechanism 1204, which, in its extended configuration, state forms the bottom of the slot into which the canister is inserted, clamps the flange of the plug securing it to the instrument. A clamp 1203 secures the shell of the canister drive mechanism 1202, and extends shaft 1201 to engage the coupling 1002. This action couples the sampling balloon to the shaft and disengages the balloon/coupling from the canister shell.

The drive mechanism 1202 then elevates the canister and balloon until it clears the plug 104, which is then retracted into the instrument. The drive mechanism 1202 lowers the balloon 1001 into the preservative solution 1502.

Mechanical energy is applied to release cells from the surface of the balloon 1001 into the preservative solution 1502. This energy may be applied by ultrasonic excitation applied to the preservative solution. In this mode, ultrasonic transducers 1504 are embedded in the clamp mechanism 1507 and ultrasonic energy is coupled through the walls of the vial 1501 into the solution 1502 which, in turn, couples that energy to the surface of the balloon 1001. Alternatively, linear and rotary oscillation can be imparted to the balloon 1001 by the drive mechanism 1202. In yet another embodiment of the invention, pneumatic excitation can be applied to the interior of the balloon 1001 via a path through the drive mechanism 1202 and the coupling 1002. The pneumatic excitation is provided in the form of pulsating air pressure (nominally less than 5 psi per pulse). The pulsating air pressure may be provided by any appropriate means known to those skilled in the art including, but not limited to reciprocating piston, peristaltic and astable air amplifier devices.

The drive mechanism 1202 then raises the balloon 1001 to above the level of the plug 1004. The plug 1004 is extended from the instrument and the clamp mechanism 1203 is released. The drive mechanism 1202 lowers the balloon 1001 and the canister shell 1003 onto the plug 1004. The drive mechanism 1202 disengages the shaft 1201 from the coupling 1002 and simultaneously engages coupling 1002 to the canister shell 1003. The drive mechanism 1202 retracts shaft 1201 leaving the assembled canister in the slot on the instrument face.

The clamp 1204 then releases, thus allowing the user to remove the canister with enclosed balloon from the instrument. The rotary decapper 1503 extends from the instrument; lowers the cap onto the vial 1501; secures the cap to the vial; elevates to clear the vial and retracts into the instrument. The clamp 1507 releases, thus allowing the user to remove the sealed vial 1501 and enclosed cell suspension from the instrument. The vial containing the cell suspension may then be processed by any relevant method known to those skilled in the art.

While the invention has been described with reference to specific embodiments, it will be apparent to those skilled in the art that many alternatives, modifications and variations may be made. Accordingly, the present invention is intended to embrace all such alternatives, modifications and variations that may fall within the spirit and scope of the appended claims.

We claim:

1. A cell analysis system comprising:
   a collector for collecting a spatially arranged cell sample from a target tissue onto a non-planar surface of the collector; and
   an analyzer that examines the cell sample for abnormal cells while the cell sample remains on the non-planar surface of the collector.

2. The cell analysis system of claim 1, wherein the cell sample is a cervical cell sample comprising endocervical cells and ectocervical cells.

3. The cell analysis system of claim 1, wherein the cell sample retains its spatial arrangement when removed from the target tissue.

4. The cell analysis system of claim 1, wherein the analyzer determines the spatial location of a group of one or more abnormal cells.

5. The cell analysis system of claim 1, wherein the analyzer differentiates between normal and abnormal cells and reports on a degree of difference therebetween.

6. The cell analysis system of claim 1, wherein the collector comprises a collection surface configured to approximate the shape of a human cervix.

7. The cell analysis system of claim 1, wherein the cell sample is analyzed on an individual cell basis.

8. The cell analysis system of claim 1, wherein the cell sample is analyzed en masse.

9. The cell analysis system of claim 1, wherein the cell sample is analyzed optically.

10. The cell analysis system of claim 1, wherein the cell sample is analyzed by analyzing the cellular fluorescence of the cell sample.

11. The cell analysis system of claim 10, wherein the cellular fluorescence is intrinsic to the cell sample.

12. The cell analysis system of claim 10, wherein the cellular fluorescence is imparted to the cell sample via an extrinsic mechanism.

13. The cell analysis system of claim 12, wherein the cellular fluorescence is imparted to the cell sample via one or more immunochemical reagents.

14. The cell analysis system of claim 12, wherein the cellular fluorescence is imparted to the cell sample via one or more chemical reagents.

15. The cell analysis system of claim 10, wherein the cellular fluorescence is analyzed according to its intensity.

16. The cell analysis system of claim 15, wherein the fluorescence intensity is measured at a plurality of wavelengths.

17. The cell analysis system of claim 1, wherein cells naturally adhered to the non-planar surface.

18. The cell analysis system of claim 1, wherein the non-planar surface is treated to enhance cell adhesion.

19. The cell analysis system of claim 1, wherein the spatial arrangement of the cellular sample is reported to an operator.

20. A cell analysis system comprising:
    a collector for collecting a spatially arranged cell sample from a target tissue; and
    an analyzer that examines the cell sample for abnormal cells while the cell sample remains on a surface of the collector, wherein the analyzer determines the spatial location of a group of one or more abnormal cells.

* * * * *